(12) United States Patent
Yadav et al.

(10) Patent No.: US 6,531,704 B2
(45) Date of Patent: Mar. 11, 2003

(54) NANOTECHNOLOGY FOR ENGINEERING THE PERFORMANCE OF SUBSTANCES

(75) Inventors: Tapesh Yadav, Longmont, CO (US); Bijan K. Miremadi, Longmont, CO (US)

(73) Assignee: NanoProducts Corporation, Longmont, CO (US)

( * ) Notice: Subject to any disclaimer, the term of this patent is extended or adjusted under 35 U.S.C. 154(b) by 0 days.

(21) Appl. No.: 09/730,053

(22) Filed: Dec. 5, 2000

(65) Prior Publication Data

US 2001/0000889 A1 May 10, 2001

Related U.S. Application Data

(63) Continuation-in-part of application No. 09/165,439, filed on Oct. 2, 1998, now Pat. No. 6,214,195.
(60) Provisional application No. 60/161,098, filed on Oct. 22, 2000, and provisional application No. 60/100,269, filed on Sep. 14, 1998.

(51) Int. Cl.[7] .............................. G21G 4/00; C30B 9/14
(52) U.S. Cl. ..................................... 250/493.1; 205/766
(58) Field of Search ....................... 204/157.15; 502/20, 502/506; 205/766; 250/493.1

(56) References Cited

PUBLICATIONS

Fotou et al., "Titania by Spray Pyrolysis for Photocatalytic Destruction of Organics in Aqueous Solutions", 5th World Congress of Chemical Engineering, vol. 4, pp. 620–625. (no month available, 1996).*

* cited by examiner

*Primary Examiner*—Edna Wong
(74) *Attorney, Agent, or Firm*—Stuart T. Langley, Esq.; Hogan & Hartson LLP

(57) ABSTRACT

Illustrations are provided on applications and usage of electrically activated catalysts. Methods are disclosed for preparing catalysts from nanomaterials. Processes and devices are described that utilize catalysts. The invention can also be applied to improve the performance of existing catalysts, to enhance the performance of substances by inducing or applying charge in nanostructured forms of substances, and to prepare novel devices. Example processes for hydrogen production are discussed. Finally, the invention can be utilized to engineer the thermal, structural, electrical, magnetic, electrochemical, optical, photonic, and other properties of nanoscale substances.

4 Claims, 7 Drawing Sheets

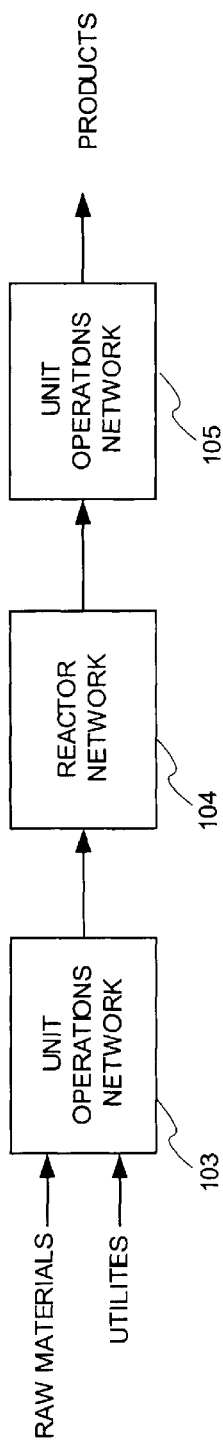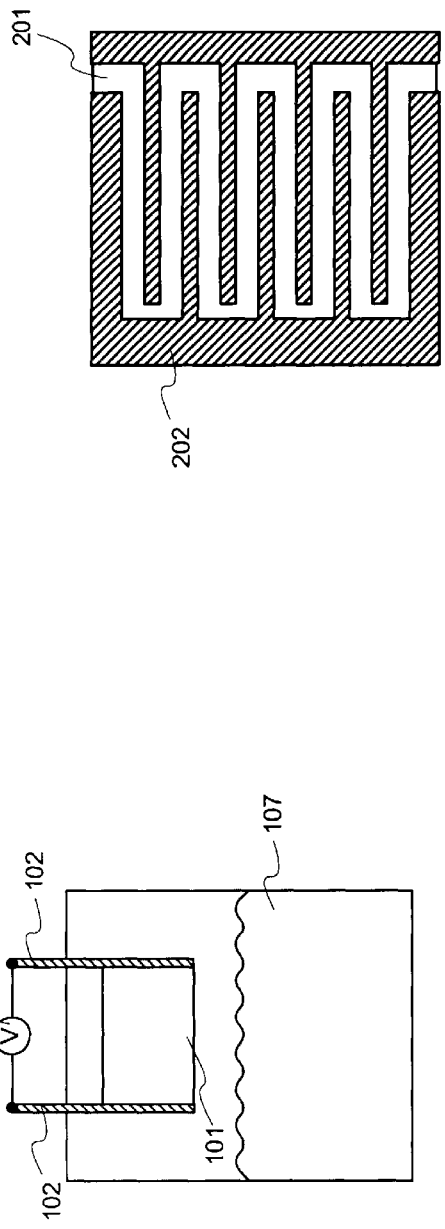

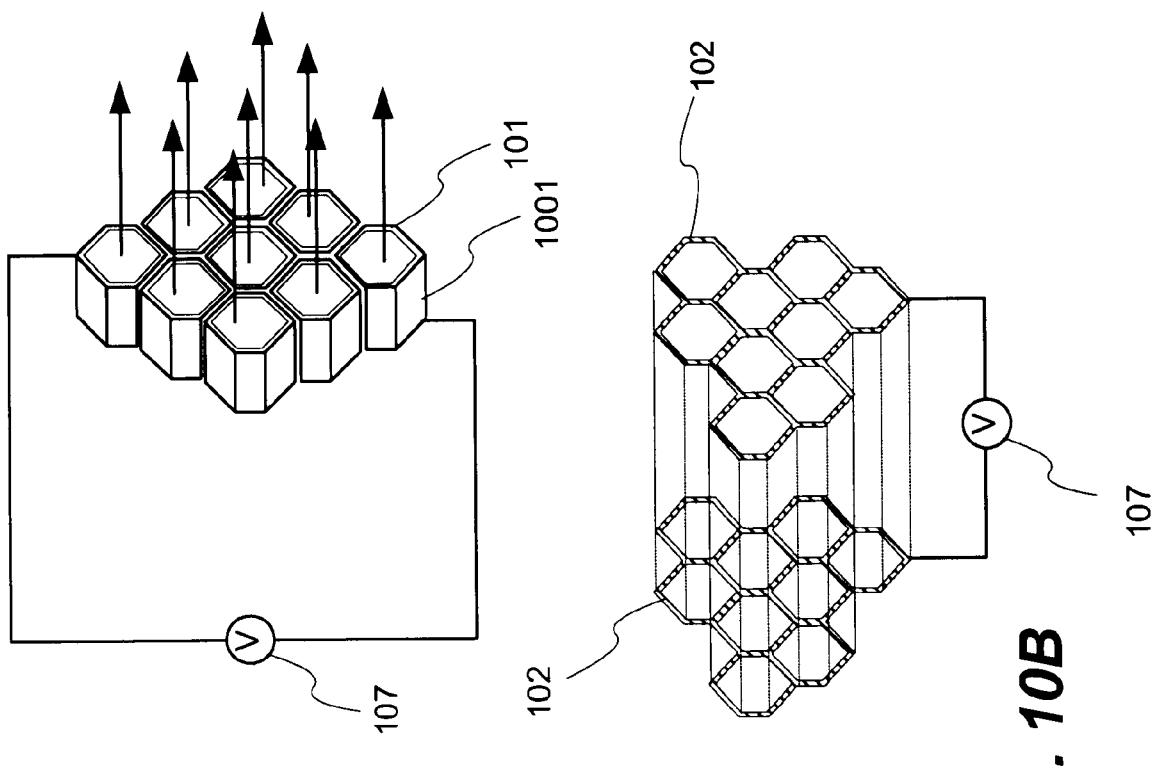

US 6,531,704 B2

NANOTECHNOLOGY FOR ENGINEERING THE PERFORMANCE OF SUBSTANCES

RELATED APPLICATIONS

This application claims benefit of commonly assigned U.S. Provisional Application No. 60/161,098 filed on Oct. 22, 2000 and is a continuation-in-part of and claims benefit and priority of commonly assigned U.S. patent application Ser. No. 09/165,439 titled "A METHOD AND DEVICE FOR TRANSFORMING CHEMICAL COMPOSITIONS" filed Oct. 2, 1998, now U.S. Pat. No. 6,214,195, which claims benefit to U.S. Provisional Application No. 60/100,269 filed Sep. 14, 1998, the specifications of which are incorporated herein by reference.

BACKGROUND OF THE INVENTION

1. Field of the Invention

The present invention relates, in general, products and processes resulting from catalytic processing, and, more particularly, from a method and apparatus for enhanced catalytic processing using catalyst compositions in an electric field.

2. Relevant Background

Chemical and materials synthesis and transformation is one of the core industries of world economy. Numerous substances are synthesized using processes that require non-ambient temperatures and/or non-ambient pressures that require capital intensive equipment. Methods that can produce useful chemicals and materials at conditions closer to ambient conditions and use simple equipment are economically, ecologically, and environmentally more desirable.

Chemical species such as volatile organic chemicals (VOCs), heavy metals in waste water and bioactive chemicals are pollutants of serious concern. A need exists for processes and devices that can convert these substances into more benign forms such as carbon dioxide and water vapor. Techniques currently in use include incineration, absorption/desorption, chemical wash and photocatalysis. Incineration is a high energy process and often leads to non-benign secondary emissions such as nitrogen oxides (NOx) and unburned hydrocarbons. Photocatalysis systems are expensive to install and require high maintenance to avoid degrading efficiencies and treatment reliability. Other techniques lead to secondary wastes and leave the ultimate fate of the pollutants unresolved. A technique is needed that can reliably treat chemical pollutants in a cost effective manner.

Numerous industries use catalytic processing techniques either to produce useful materials and compositions or to reduce waste or pollutants. Examples of such industries include those based on electricity generation, turbines, internal combustion engines, environmental and ecological protection, polymer and plastics manufacturing, petrochemical synthesis, specialty chemicals manufacturing, fuel production, batteries, biomedical devices, and pharmaceutical production. These industries are in continuous need of new catalysts and catalytic processes that can impact the costs and performance of the products generated by these industries.

Currently, processes and methods based on homogeneous and heterogeneous catalysis are integral and important to modern industrial, energy, and environmental chemistry. In petroleum and petrochemical industries, catalysis is used in numerous purification, refining, cracking, and/or reaction steps. In the purification of synthetic gaseous and liquid fuels from crude oil, coal, tar sand, and oil shale, catalysis is important. Approximately two thirds of leading the large tonnage chemicals are manufactured with the help of catalysis. Illustrative examples include acetic acid, acetaldehyde, acetone, acrylonitrile, adipic acid, ammonia, aniline, benzene, bisphenol A, butadiene, butanols, butanone, caprolactum, cumene, cyclohexane, cyclohexanone, cyclohexanol, phtalates, dodecylbenzene, ethanol, ethers, ethylbenzene, ethanol, methanol, ethylbenzene, ethylene dichloride, ethylene glycol, ethylene oxide, ethyl chloride, ethyl hexanol, formaldehyde, hydrogen, hydrogen peroxide, hydroxylamine, isoprene, isopropanol, maleic anhydride, methyl amines, methyl chloride, methylene chloride, nitric acid, perchloroethylene, phenol, phthalic anhydride, propylene glycol, propylene oxide, styrene, sulfur, sulfuric acid, acids, alkalis, terephthalic acid, toluene, vinyl acetate, vinyl chloride, and xylenes.

Further, most of the production of organic intermediates used to make plastics, elastomers, fibers, pharmaceuticals, dyes, pesticides, resins, and pigments involve catalytic process steps. Food, drinks, clothing, metals, and materials manufacturing often utilizes catalysts. Removal of atmospheric pollutants from automobile exhausts and industrial waste gases requires catalytic converters. Liquid wastes and stream also are routinely treated with catalysts. These applications need techniques, methods, and devices that can help research, identify, develop, optimize, improve, and practice superior performing catalysts of existing formulations, of evolved formulations, and of novel formulations.

Many new products are impractical to produce due to high manufacturing costs and/or low manufacturing yields of the materials that enable the production of such products. These limitations curtail the wide application of new materials. Novel catalysts can enable the production of products that are currently too expensive to manufacture or impossible to produce for wide ranges of applications that were, until now, cost prohibitive. A need exists for techniques to develop such novel catalysts.

The above and other limitations are solved by a chemical transformation device and method for processing chemical compositions that provides efficient, robust operation yet is implemented with a simplicity of design that enables low cost implementation in a wide variety of applications. These and other limitations are also solved by a method for making a chemical transformation device using cost efficient processes and techniques.

SUMMARY OF THE INVENTION

In one aspect, the invention includes processes and products using a method of chemically transforming a substance through the simultaneous use of a catalyst and electrical current. This method comprises selecting an active material which interacts with an applied electromagnetic field to produce a current. A high surface area (preferably greater than 1 square centimeter per gram, more preferably 100 square centimeter per gram, and most preferably 1 square meter per gram) form of the active material is prepared. The active material is formed into a single layer or multilayered structure that is preferably porous. The stream containing substance that needs to be transformed is exposed to the active material structure while charge flow is induced by the applied electromagnetic field. Where appropriate, the product stream is collected after such exposure.

In a related aspect, the invention comprises a method of manufacturing a device comprising an active material preferably with high band gap (preferably greater than 0.5 eV, more preferably 1.5 eV, most preferably 2.5 eV). The active material is preferably provided a high surface area form such as a nanostructured material or a nanocomposite or a high internal porosity material. A porous structure comprising at least one layer, such as a thin film layer, of the active material and electrodes positioned on the at least one layer to enable an electromagnetic field to be applied across the at least one layer. It is preferred that the resistance of the device between the electrodes be between 0.001 milliohm to 100 megaohm per unit ampere of current flowing through the device, more preferably between 0.01 milliohm to 10 megaohm per unit ampere of current flowing through the device, and most preferably 1 milliohm to 1 megaohm per unit ampere of current flowing through the device.

In case the current flow measure is not known or difficult to measure, it is preferred that the corresponding power consumption levels for the device be used to practice this invention. To illustrate, in case of electromagnetic field is externally applied, then it is preferred that the power consumption due to device operation be between 0.001 milliwatt to 100 megawatt. While miniature, thin film, and micromachined devices may utilize power less than these and applications may use power higher than these levels, and such applications are herewith included in the scope of this invention, in all cases, design and/or operation that leads to lower power requirement is favored to minimize the operating costs by the device. Higher resistances may be used when the chemical transformation step so requires. In case, alternating current is used, the overall impedance of the device must be kept low to reduce energy consumption and operating costs. Once again, the yield, the selectivity, the operating costs and the capital costs of the device must be considered in designing, selecting, and operating the device.

Previous studies have used electrochemical and electrolytic techniques for converting certain species into more desirable species. As an illustration, a voltage when applied across a solid electrolyte (for example an ion conducting membrane) have been reported to cause reversible increases in catalytic activity and changes in selectivity of metals supported on the electrolyte. These results have been explained using the non-Faradaic electrochemical modification of catalytic activity (NEMCA) effect. The present invention is distinct from these studies in at least the following ways:

(1) an electromagnetic field (e.g. voltage) is applied to the catalyst itself, as opposed to an electrolyte, using an external circuit and this causes the current to flow in the catalyst;

(2) reversing the polarity of the electrodes to the catalyst does not change the reaction kinetics or selectivity. Alternatively alternating, sinusoidal, or other types of pulsating currents may be used for embodiments taught herein whereas (3) current is not needed all the times and may just be used to activate the catalyst in desirable ways, and (4) reaction takes place on the low impedance catalyst which may be supported by a porous and relatively higher impedance substrate, while electrical current passes through the catalyst. In contrast, for NEMCA effect the substrate (electrolyte) is necessarily conducting.

In another aspect, the present invention provides methods to efficiently provide localized thermal or activation energy at the surface of a catalyst. Additionally, the present invention offers a method of reducing or preventing the need for external thermal energy input.

In another aspect the present invention provides processes that produce superior performing and environmentally benign manufacturing of products through the quench of undesired secondary reactions.

In a related aspect the present invention provides process of developing catalysts and products derived using these catalysts.

In another aspect, the present invention provides a process of producing useful products from raw materials through the simultaneous use of a catalytic surface that stationary with respect to the raw material being processed and an induced field inside the catalyst.

In yet another aspect, the present invention provides methods for the preparation of a device for chemically transforming a species through the use of electromagnetic field. Additionally, the present invention describes products prepared using such devices for chemically transforming a species with electromagnetic field. In another aspect, the present invention describes applications of novel fluid and chemical composition transformation technique.

METHOD OF OPERATION

An exemplary process in accordance with the present invention is operated by first pre-treating a feed composition in a way that changes the free energy of the feed composition to a more desirable state. To illustrate, but not limit, the feed composition may be heated or cooled, pressurized or depressurized, mixed, sparged, evaporated partially or fully, filtered, decanted, crushed into finer particle sizes, emulsified, bio-activated, partially or fully combusted, or separated into desired chemistry using any technique.

Optionally, the pre-treated feed is then either combined with similarly pre-treated feed or untreated feed. The component feeds (i.e., pre-treated feed(s) and untreated feed(s) are preferably thoroughly mixed, but may be mixed to any desired degree. The combination ratios between component feed compositions can be varied widely to meet the needs of a particular application. The resultant feed is then passed over a device comprising of an active material.

The device is operated by placing the active material in a direct current or alternating current electrical circuit that leads to flow of charge. The charge flow can be through flow of electrons, flow of ions, or flow of holes. In one embodiment, it is preferred that during operation, the circuit be switched on first such that charges begin to flow in the circuit. Next, feed material is exposed to the active material for duration desired and the products resulting from such exposure are collected. In another embodiment it is preferred that the feed material be in contact with the active material catalyst first, next the flow of charge is initiated by switching on the electrical circuit. In yet another embodiment, the circuit is switched on to induce flow of charge that initiates the desired reaction which is then followed by changing the electromagnetic field that best favors the performance of the catalyst, the yield, the selectivity, the operating costs and the capital costs of the device. In another embodiment, the circuit is operating in a time varying or pulsating or pre-programmed switching on and off of the electrical circuit to induce corresponding flow of charge through the active material.

In one or more embodiments, the device may be cooled or heated using secondary sources, pressurized or evacuated using secondary sources, photonically and optically activated or isolated using secondary sources, laser activated or field influenced using secondary sources, gas, liquid, solid, ion, or energy influenced using secondary sources. The device may be heated or cooled to desired temperature through resistive or convective or radiative heating for illustration, pressurized or evacuated to desired pressure through piezo effects for illustration, photonically and optically activated to desired photonic influence through phosphorescence affects for illustration. The device may assist such functions by design through the use of the electrical current directly, i.e. the current affects the catalyst and also enables such desired state variables. The device may be free standing or fully supported or partially supported. The device may be operated in steady state, unsteady state, pulsed mode, continuous or batch mode, symmetric waveforms, asymmetric waveforms, in motion or in stationary state. The products from the device are then removed from the neighborhood of the device, collected, and distributed.

In some embodiments, the heating or cooling from the device or unit operations described in this invention may be usefully applied. To illustrate, if the device is being cooled, the heat so extracted may be used to heat another process stream or a space such as the passenger cabin of a car or home.

In another embodiment, the catalytic properties of a substance are modified because of the electromagnetic potential applied to the substance. In such cases, the potential may be applied by an external circuit containing the substance, or the potential may be applied due the presence of another substance which induces a potential because of proximity and difference in chemical potential between the substances. To illustrate the later but not limit, if cobalt nanoparticles were to be intimately mixed with gold nanoparticles, the difference in the chemical potential would induce a charge in the nanoparticles. This charge would induce cobalt interfacial atoms of the cobalt nanoparticles to exhibit nickel like catalytic behavior and gold interfacial atoms of the gold nanoparticles to exhibit platinum like catalytic behavior.

BRIEF DESCRIPTION OF THE DRAWINGS

FIG. 1A and FIG. 1B show alternative views of a mechanism implementing a process in accordance with the present invention;

FIG. 2 shows a schematic view of a preferred alternative chemical transformation device in accordance with the present invention;

FIG. 10A and FIG. 10B show an exemplary support structure in accordance with one embodiment of the present invention.

DETAILED DESCRIPTION OF THE PREFERRED EMBODIMENTS

Figure 3:
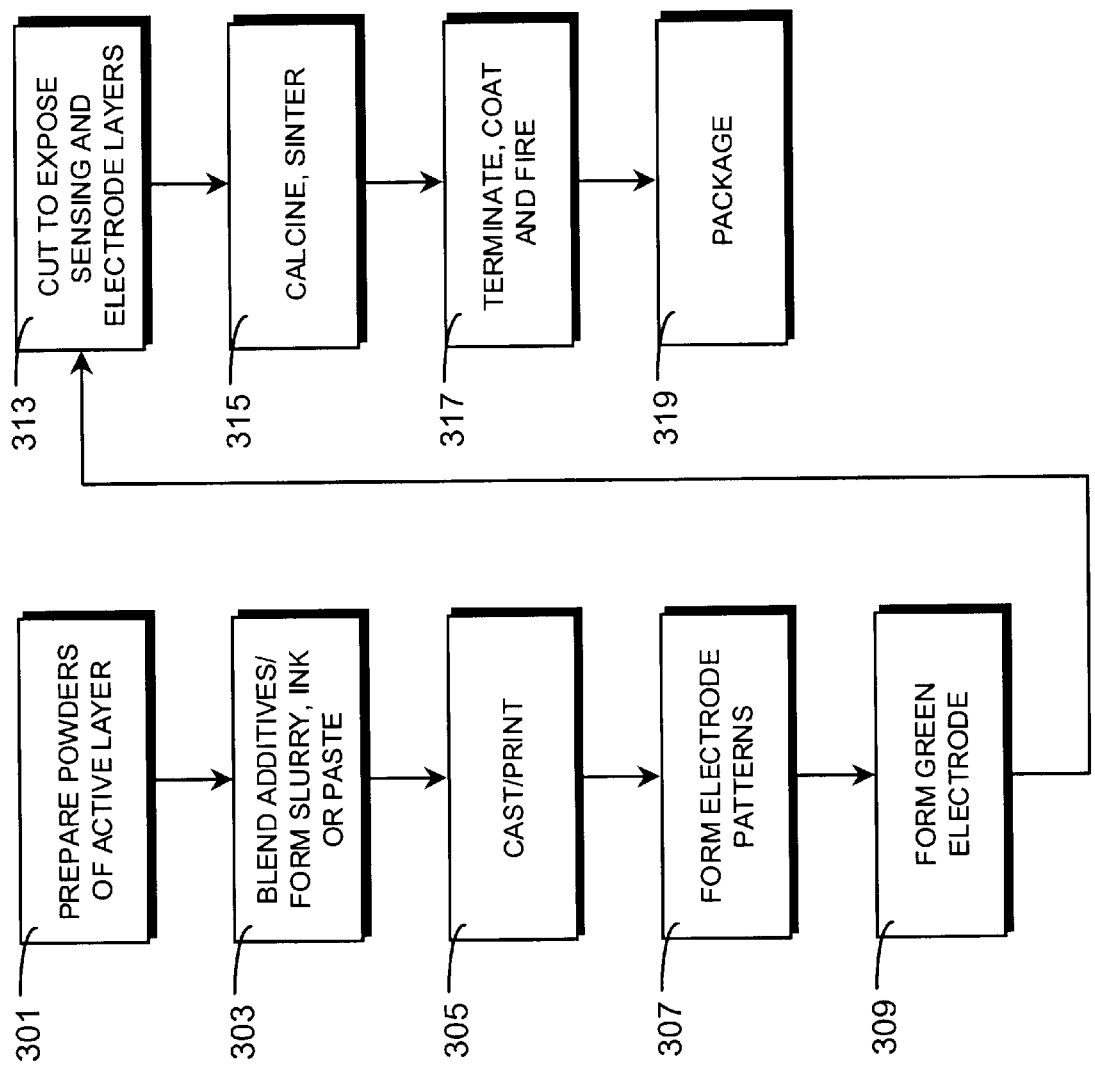
FIG. 3 shows a flow diagram of major steps in a process in accordance with the present invention.

The present invention involves all phases of catalytic processing including devices for performing catalytic processing, methods of making devices for catalytic processing, and methods for operating devices to perform catalytic processing. The present invention is described in terms of several specific examples but it is readily appreciated that the present invention can be modified in a predictable manner to meet the needs of a particular application. Except as otherwise noted herein, the specific examples shown herein are not limitations on the basic teachings of the present invention but are instead merely illustrative examples that aid understanding.

Specific examples in this specification involve application of high surface area catalysts on porous structures such as, but not limiting to honeycomb structured substrates. This technique in accordance with the present invention reduces the thermal mass of the catalytic system comprising the catalyst and its supporting structure. It has been found that catalytic behavior is significantly enhanced by procedures and structures that reduce the system's thermal mass while increasing surface area of the catalyst. The specification suggests reasons why the various examples behave in the manner observed, however, these explanations provided to improve understanding are not to be construed as limitations on the teachings of the present invention.

The present invention is described using terms of defined below:

"Catalysis," as the term used herein, is the acceleration of any physical or chemical or biological reaction by a small quantity of a substance-herein referred to as "catalyst"-the amount and nature of which remain essentially unchanged during the reaction. Alternatively, the term, includes applications where the catalyst can be regenerated or its nature essentially restored after the reaction by any suitable means such as but not limiting to heating, pressure, oxidation, reduction, and microbial action. For teachings contained herein, a raw material is considered catalyzed by a substance into a product if the substance is a catalyst for one or more intermediate steps of associated physical or chemical or biological reaction.

"Chemical transformation," as the term used herein, is the rearrangement, change, addition, or removal of chemical bonds in any substance or substances such as but not limiting to compounds, chemicals, materials, fuels, pollutants, biomaterials, biochemicals, and biologically active species. The terms also includes bonds that some in the art prefer to not call as chemical bonds such as but not limiting to Van der Waals bonds and hydrogen bonds.

"Nanomaterials," as the term is used herein, are substances having a domain size of less than 250 nm, preferably less than 100 nm, or alternatively, having a domain size sufficiently small that a selected material property is substantially different (e.g., different in kind or magnitude) from that of a micron-scale material of the same composition due to size confinement effects. For example, a property may differ by about 20% or more from the same property for an analogous micron-scale material. In case the domain size is difficult to measure or difficult to define such as in porous networks, this term used herein refers to substances that have interface area greater than 1 square centimeter per gram of the substance. The ratio of the maximum domain dimension to minimum domain dimension in the catalyst for this invention is greater than or equal to 1. The term nanomaterials includes nanopowders, nanoparticles, nanofilms, nanofibers, quantum dots, and the nanomaterials may be coated, partially coated, fully coated, island, uncoated, hollow, porous, and dense domains. Furthermore, nanomaterials may be produced by any method to practice this invention.

"Domain size," as the term is used herein, is the minimum dimension of a particular material morphology. The domain size of a powder is the grain size. The domain size of a whisker or fiber is the diameter, and the domain size of a film or plate is the thickness.

"Confinement size" of a material, as the term is used herein in reference to a fundamental or derived property of interest, is the mean domain size below which the property becomes a function of the domain size in the material.

"Activity" of a catalyst, as the term used herein, is a measure of the rate of conversion of the starting material by the catalyst.

"Selectivity" of a catalyst, as the term used herein, is a measure of the relative rate of formation of each product from two or more competing reactions. Often, selectivity of a specific product is of interest, though multiple products may interest some applications.

"Stability" of a catalyst, as the term used herein, is a measure of the catalyst's ability to retain useful life, activity and selectivity above predetermined levels in presence of factors that can cause chemical, thermal, or mechanical degradation or decomposition. Illustrative, but not limiting, factors include coking, poisoning, oxidation, reduction, thermal run away, expansion-contraction, flow, handling, and charging of catalyst.

"Porous" as used herein means a structure with sufficient interstitial space to allow transport of reactant and product materials within the structure to expose the reactant materials to the constituent compositions making up the porous structure.

"Electrically activated catalysis," as the term is used herein, means providing a quantity of a catalyst, exposing a feed substance to the quantity of catalyst, inducing or providing a flow of charge inside the quantity of catalyst by applying an electromagnetic field across the catalyst during the exposure to a feed stream for a period sufficient to initiate a desired tranformation in the feed substance.

"Electrically activated catalyst," as the term is used herein, is the catalyst used in electrically activated catalysis.

FIG. 1 illustrates an embodiment of the present invention in a basic form. Essentially, feed material or waste material is, if needed, pre-treated using a subsystem consisting of one or more unit operations such as those identified in 103. These include, for example, heat exchangers, distillation, extraction, condensation, crystallization, filtration, drying, membrane pumps, compressors, separation, expanders and turbines that function to modify the physical, chemical and/or electrical state of the raw materials using available processing techniques.

The pretreated feed is then processed through one or more catalytic device(s) 101 within reactor network 104 where desirable transformations occur. The product from reactor network 104 is, if desired, post-treated using a subsystem consisting of one or more unit operations such as those identified in 105. In an alternative shown in FIG. 1B. catalytic device 101 is placed in contact with a gaseous, liquid, solid, or mixed phase feed 107 and the desirable transformation(s) occur. The catalytic device 101 is coupled across a source of electromagnetic energy such as, for example, power supply 106 by conductive electrodes 102. The feed composition is contained in an appropriate container, and the catalytic device is arranged within the container to contact the gaseous form of the feed 107 as shown in FIG. 1B, or may be submerged or enveloped in a solid or mixed-phase form or the feed 107 with straightforward modifications.

FIG. 2 illustrates the catalytic device in an embodiment of the present invention in a basic form. Essentially, an active layer 201 is sandwiched between two electrodes 202. Active layer 201 comprises a material that either as applied or as later modified by postprocessing acts as a catalyst for to convert a particular feed composition into a desired product composition. The dimensions and geometry of active layer 201 are selected to provide both sufficient exposure to a feed composition (i.e., a composition that is to be catalyzed) and to allow an impeded current flow between electrodes 202 when an electromagnetic field is applied across electrodes 202.

Although specific examples of materials suitable for active layer 201 are set out below, active layer 201 more generally comprises a material that is an active catalyst for a desired reaction when activated by an applied electric field. The properties of active layer 201 are selected to allow active layer 201 to both support an electric field and conduct current. It is not necessary that active layer 201 be active as a catalyst at ambient conditions (e.g., without applied electromagnetic field). However, in some embodiments, the active layer 201 may have catalytic activity in ambient or non-ambient conditions even when an electric field is not applied between electrodes 202.

A method for preparing a chemical composition transformation device in accordance with the present invention involves selecting an active material comprising a surface that physically, chemically, or biologically interacts with the substance that is desired to be transformed or with one of the intermediates of such substance. The active material is preferably prepared in a high surface area form (i.e., a form that exhibits a surface area of preferably greater than 1 square centimeter per gram, more preferably 100 square centimeter per gram, and most preferably 1 square meter per gram). It is believed that the present invention is enhanced by the interaction between the surface area of particles making up the active layer 201 and the applied electromagnetic field. Accordingly, a higher surface area form tends to increase desirable catalytic behavior for a given quantity of material.

By way of explanation, the inventors have noted that electromagnetic fields in the form of voltage and/or current gradients across a nanostructured material manifest markedly different effects as compared to fields of similar magnitude applied across materials with larger particle size. In conventional devices, materials exist either in an atomic state or in a bulk state. Larger particle sizes (e.g., particles larger than the critical domain size of the material) behave as bulk materials under exposure to electromagnetic fields. While an explanation of these unexpected effects is beyond the scope of this specification, it is contemplated that the interaction of particle sizes less than the critical domain sizes of a material result in surprisingly unusual interaction between particles and/or creation of an electronic state at a nanoscopic level that differs from either the materials in atomic form or the materials in bulk form.

FIG. 3 illustrates basic steps in an exemplary process for manufacturing a catalytic device in accordance with the present invention. The active material, usually prepared as a powder or powder mixture in step 301 and then optionally blended with additional compositions to form a slurry, ink or paste for screen printing in step 303. In step 305 the active material is directly or alternatively formed into a film, pellet, or multilayer structure comprising the active material. The film, pellet, or multilayer structure may be prepared as free standing or on a substrate. In case of multilayer structure, dielectric or ferromagnetic layers may be utilized to modify or induce a field in the active layers.

The active layer structure may be porous or the structure may be non-porous. It is preferred that the device be porous to reduce pressure drop and enhance contact of the active element with the chemical species of interest. Table 1 lists some catalysts and pore size ranges to illustrate but not limit the scope:

TABLE 1

Catalyst Types and Pore Sizes

| (1) Catalyst | Average Pore Radius (Å) |
|---|---|
| Activated carbons | 10–20 |
| Silica gels | 15–100 |
| Silica-alumina cracking catalysts ~ 10–20% Al$_2$O$_3$ | 15–150 |
| Silica-alumina (steam deactivated) | 155 |
| Silica-magnesia microsphere: Nalco, 25% MgO | 14.3 |
| Da-5 silica-magnesia | 11.1 |
| Activated clays | ~100 |
| TCC clay pellets (MgO, CaO, Fe$_2$O$_3$, SO$_4$) = ~10% | 26.3 |
| Clays: | |
| Montmorrillonite (heated 550° C.) | 25.2 |
| Vermiculite | ~314 |
| Activated alumina (Alorico) | 45 |
| CoMo on alumina | 20–40 |
| Kieselguhr (Celite 296) | 11,000 |
| Fe-synthetic NH$_3$ catalyst | 200–1000 |
| Co—ThO$_2$-Kieselguhr 100:18:100 (reduced) pellets | 345 |
| Co—ThO$_2$—MgO (100:6:12) (reduced) granular | 190 |
| Co-Kieselguhr 100:200 (reduced) granular | 2030 |
| Porous plate (Coors No. 760), Pumice, Fused Copper Catalyst, Ni Film, Ni on Pumice | 2150 |

In other embodiments, the structure may be smooth or wavy, flexible or rigid, homogeneous or heterogeneous, undoped or doped, flat or cylindrical or any other shape and form, nanostructured or non-nanostructured. In all cases, this invention prefers that the material compositions chosen be physically robust in presence of all species in its environment in particular and all environmental variables in general for a duration equal to or greater than the desired life for the device. In all cases, this invention requires that the material selected has a finite impedance in the presence of electromagnetic field.

Once a suitable material composition has been selected for use in the chemical composition transformation device, in one embodiment, namely the formation of a chemical composition transformation device, a disc or body or single active layer laminated stack structure is formed, or in another embodiment a multilayer structure (as shown in FIG. 2) is formed in step 305 from the selected active material.

The active material layer formed in step 305 or structure or device form can be formed by any method or combination of methods, including but not limited to spin coating, dip coating, surface coating a porous structure, powder pressing, casting, screen printing, tape forming, precipitation, sol-gel forming, curtain deposition, physical sputtering, reactive sputtering, physical vapor deposition, chemical vapor deposition, ion beam, e-beam deposition, molecular beam epitaxy, laser deposition, plasma deposition, electrophoretic deposition, magnetophoretic deposition, thermophoretic deposition, stamping, cold pressing, hot pressing, explosion, pressing with an additive and then removal of the additive by heat or solvents or supercritical fluids, physical or chemical routes, centrifugal casting, gel casting, investment casting, extrusion, electrochemical or electrolytic or electroless deposition, screen-stencil printing, stacking and laminating, brush painting, self-assembly, forming with biological processes, or a combination of one or more of the above-mentioned methods.

The active material can be in film form or dispersed particle form or bulk form or wire form. The cross section area of the active material structure can be few microns square to thousands of meters square depending on the needs of the application. In a preferred embodiment, the active material can also be doped with available promoters and additives to further enhance the device's performance. In another preferred embodiment, the active material can also be mixed with inert elements and compositions and insulating formulations to further reduce capital or operating costs such as those from raw materials and pressure drop.

In a preferred embodiment, the catalyst is applied in a form and structure that minimizes the thermal mass of the system. In this regard, the catalyst and any supporting substrate(s) are considered components of the system. A given system's effectiveness is related to the surface area of catalyst that participates in the reaction. Thin film or thick film catalyst layers provide large surface area compared to bulk or pellet forms using a smaller amount of catalyst.

In a specific implementation illustrated in FIG. 10A and FIG. 10B, a substrate 1001 such as a ceramic honeycomb, for example, supports electrodes 102 and catalyst layer or layers 101. A variety of ceramic honeycomb support structures 1001 are available ranging in shape from screens and grids, to polygon-celled matrices, to coiled structures that resemble corrugated cardboard, to porous ceramic with multiple heterogeneously- or regularly-shaped cells. Each of these structures enable a catalyst 101 to be coated onto some or all surfaces of the support 1001 using deposition or thin film techniques to some or all surfaces while enabling a fluid stream to pass through the structure with high exposure to the catalyst as suggested by the arrows in FIG. 10A. The catalytic support may be ceramic or any other composition consisting of elements from the periodic table and composites thereof. The honeycomb may be of various pore sizes, pore size distributions, pore shapes, pore morphology, pore orientation, pore lattices, composition, size, and may be manufactured by any method. To illustrate, the honeycomb may have bee-like hexagonal pore shape and each layer of the pore may be aligned with the layer above it. Alternatively the honeycomb may have circular pore shape and each layer may center at the edge of the layer above it. Numerous other configurations may be applied to maximize the efficiency and effectiveness of the catalytic process.

Electrodes 102 can be affixed to the catalyst coated honeycomb structure, for example, at the front and back of the structure (with respect to the pore opening) as suggested in FIG. 10B in a manner that enables an electromagnetic field (e.g. a voltage gradient or current flow) to be imposed substantially equally across the catalyst coating. Electrodes can be affixed to the catalyst 101 using thin or thick film techniques. Other electrode configurations may be equivalently substituted to meet the needs of a particular application so long as the electrodes when energized by a power supply 106 apply an electromagnetic field across the catalyst 101 itself. Care should be taken to ensure that the applied electromagnetic field is actually realized in the catalyst 101 and not dissipated by the support structure 1001. For this reason, relatively non-conductive materials are preferred for support structure 1001. In the case of magnetically induced electromagnetic fields, a non-permeable material may be preferred for support structure 1001.

In contrast to bulk or pellet or film catalyst shapes, honeycomb catalyst layers maximize the potential contact of gases and active species such as radical while reducing the mass of catalyst needed which can reduce the capital cost of catalyst. Furthermore, it is preferred that the phonon pathways be minimized to reduce heat loss. One method of accomplishing this is to coat any and all surfaces of a honeycomb substrate. Another method is to produce a honeycomb structure from the catalytic material directly, with or without dopants; some, but not limiting, illustrations of such produce would be aerogels, hydrogels, imprint cast material. These techniques reduce the electrical energy needed to keep the catalyst at a given temperature and given operating condition. Less thermal mass and smaller area for conductive or convective or radiative thermal transport can decrease the cost of electrical energy needed for given yield or selectivity. The porosity of the honeycomb may be varied both in size and the density of pores and it is anticipated that the porosity characteristic may be different for different chemistries.

These examples illustrate the utility of catalyst films in the practice of field assisted transformation of chemical and material compositions. Catalyst supported on honeycomb examples exhibit improved efficiency in converting chemical compositions from a feed product to an end product. It is contemplated that a wide variety of electrode patterns, substrate compositions, membrane compositions, and catalyst materials will benefit from the utility of these features of the present invention.

In another preferred embodiment, the active layer comprises functional materials such as those that provide thermal, sensing, pressure, charge, field, photons, structural, regeneration or other needed functions. Secondary treatments of the active material through sintering, pressurization, doping, chemical reactions, solid state reaction, self-propagating combustion, reduction, oxidation, hydrogenation, and such treatments may enhance the performance of the active layer.

Possible compositions of the active material include but are not limited to one or more of the following materials: dielectrics, ferrites, organics, inorganics, metals, semimetals, alloy, ceramic, conducting polymer, non-conducting polymer, ion conducting, non-metallic, ceramic—ceramic composite, ceramic-polymer composite, ceramic-metal composite, metal-polymer composite, polymer—polymer composite, metal—metal composite, processed materials including paper and fibers, and natural materials such as mica, percolated composites, powder composites, whisker composites, or a combination of one or more of these. Illustrative formulations include but are not limited to doped or undoped, stoichiometric or non-stoichiometric alloy or compound of s-, p-, d-, and f-group of periodic table. Illustrative compositions that can be utilized in this invention as is or on substrates include one-metal or multi-metal oxides, nitrides, carbides, borides, indium tin oxide, antimony tin oxide, rare earth oxides, silicon carbide, zirconium carbide, molybdenum carbide, bismuth telluride, gallium nitride, silicon, germanium, iron oxide, titanium boride, titanium nitride, molybdenum nitride, vanadium nitride, zirconium nitride, zirconium boride, lanthanum boride, iron boride, zirconates, aluminates, tungstates, carbides, silicides, borates, hydrides, oxynitrides, oxycarbides, carbonitrides, halides, silicates, zeolites, self-assembled materials, cage structured materials, fullerene materials, nanotube materials, phosphides, nitrides, chalcogenides, dielectrics, ferrites, precious metals and alloys, non-precious metals and alloys, bimetal and polymetal systems, ceramics, halogen doped ceramics (such as, but not limiting to fluorine doped tin oxide), stoichiometric or non-stoichiometric compositions, stable and meta-stable compositions, dispersed systems, dendrimers, polymers, enzymes, organometallics, bioactive molecules, and mixtures thereof. Some specific, but not limiting, examples are listed in Table 2A, 2B, and 2C.

TABLE 2A

Illustrative Metals and Semimetals

| Ru | Rh | Pd | Ag |
|----|----|----|----|
| Os | Ir | Pt | Au |
| Re | W  | Zn | Hg |
| Fe | Co | Ni | Cu |
| Pb | Bi | Sb | Sn |
| Te | Se | As | Cd |
| Mo | Ti | Zr | Ce |

TABLE 2B

Illustrative Alloys

| Catalyst | Added Metal to Form Alloy | Illustrative Reaction |
|----------|---------------------------|------------------------|
| Pt | 5–20% Rh | ammonia oxidation |
| Ag | Au | ethylene oxidation |
| Ag | 10% Au | cumene oxidation |
| Pt | Ge, Sn, In, Ga | dehydrogenation and cracking of alkanes |
| Pt | Sn + Re | dehydrocyclization and aromatization of alkanes |
| Pt | Pb, Cu | dehydrocyclization and aromatization of alkanes |
| Pt, Pd, Ir | Au | oxidative dehydrogenation of alkanes; n-butene • butadiene, methanal • formaldehyde |
| Ru, Os | Cu (Ag) | catalytic reforming |
| Ir | Au (Ag, Cu) | catalytic reforming of alkanes and cycloalkanes |
| Pd |  | alkaned dehydrogenation and dehydrocyclization |

TABLE 2C

Illustrative Oxide Ceramics

| CaO, SrO, BaO | $WO_3$, $UO_3$ | NiO, $Cu_2O$, CuO | HgO, $PbO_2$, $Bi_2O_5$ |
|---|---|---|---|
| $Al_2O_3$, $SiO_2$, $P_2O_5$ | $Ta_2O_5$, $HfO_2$ | FeO, CoO, $Co_3O_4$, | $Cr_2O_3$, MnO, $Fe_3O_4$ |
| BeO, $B_2O_3$, MgO | $Nb_2O_5$, $MoO_3$ | CdO, $SnO_2$, $Sb_2O_5$, | ZnO, $GeO_2$, $As_2O_5$ |
| $Al_2O_3$—$SiO_2$ | $HfO_2$, $Fe_2O_3$ | $ZrO_2$—$SiO_2$ | $Sc_2O_3$, $TiO_2$ |
| BeO—$SiO_2$ | $ZrO_2$, $V_2O_5$ | $Y_2O_3$—$SiO_2$ | $La_2O_3$—$SiO_2$ |
| $Ga_2O_3$—$SiO_2$ | MgO—$SiO_2$ | $SnO_3$—$SiO_2$ | $Sb_3O_3$—$SiO_2$ |

Additionally, the formed active layer 201 can be porous or non-porous, flat or tapered, uniform or non-uniform, planar or wavy, straight or curved, non-patterned or patterned, micron or sub-micron, micromachined or bulk machined, grain sized confined or not, homogeneous or heterogeneous, spherical or non-spherical, unimodal or polymodal, or a combination of one or more of these.

In a preferred embodiment, the electrode structures may comprise any composition with a lower impedance than the active material composition. The composition of the electrode layer can include, but is not limited to, organic materials, inorganic materials, metallic, alloy, ceramic, polymer, non-metallic, ceramic—ceramic composite, ceramic-polymer composite, ceramic-metal composite, metal-polymer composite, polymer—polymer composite, metal—metal composite, or a combination of one is or more of these. Geometries may be porous or dense, flat or tapered, uniform or non-uniform, planar or wavy, straight or curved, non-patterned or patterned, micron or sub-micron, grain size confined or not, or a combination of one or more of these.

In the exemplary implementation outlined in FIG. 3, electrodes 102 and 202 are formed by available press/coat/mask/print techniques in step 309 followed by formation of green electrode layer(s) using, for example, printing techniques. Alternative methods of forming the electrode layers 102 and 202 include any method including but not limited to spin coating, dip coating, surface coating a porous structure, powder pressing, casting, screen printing, tape forming, curtain deposition, physical sputtering, reactive sputtering, physical vapor deposition, chemical vapor deposition, ion beam, e-beam deposition, molecular beam epitaxy, laser deposition, plasma deposition, electrophoretic deposition, magnetophoretic deposition, thermophoretic deposition, stamping, cold pressing, hot pressing, pressing with an additive and then removal of the additive by heat or solvents or supercritical fluids, physical or chemical routes, placing metal plates or films on certain parts of the active material, inserting wire, chemically transforming section in the active layer, centrifugal casting, gel casting, investment casting, extrusion, electrochemical deposition, screen-stencil printing, stacking and laminating, brush painting, self-assembly, forming with biological processes, or a combination of one or more of the above-mentioned methods.

After preparation of the stack, the stack may for some applications be cut cross sectionally into thin slices in step 313 to expose the layers of the active layer and the electrode. In another embodiment, one or more of step 307, step 309, and step 313 may be skipped. In such cases, it is necessary that the equipment containing the catalytic device provide external electrodes or equivalent means in some form to enable the flow of charge through the active material. Finally, given the catalytic properties of the active layer, some of the steps in FIG. 3 may be assisted or accomplished through the use of said catalytic properties.

Figure 4:
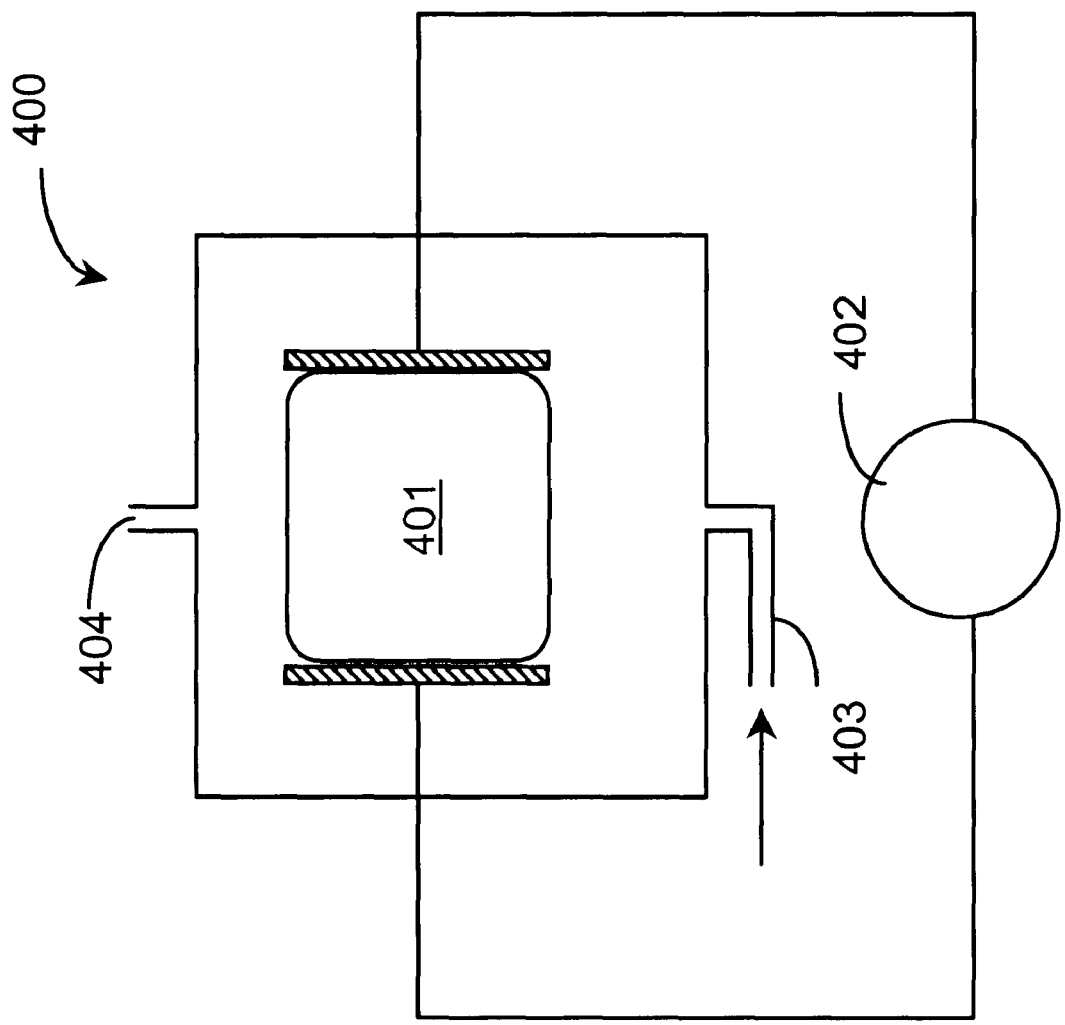
FIG. 4 shows a schematic view of a chemical transformation reactor in accordance with the present invention.

Each slice obtained from step 313 in FIG. 3 is a device that can be used in a circuit shown as FIG. 4 to transform one or more species in a gas, vapor, liquid, supercritical fluid, solid or a combination of these. In step 315 the stack is calcined or sintered to reach structural robustness, consistency, and performance in the active material and green electrode layers.

In one embodiment, the device is terminated by forming an electrical coupling to electrodes 202, 302 in step 317 enabling application of an external electrical field. In a preferred embodiment, it is desirable that the active material and the electrode layers be isolated from external environmental damage such as that from thermal, mechanical, chemical, electrical, magnetic, or radiation effects, or a combination of one or more of these. This desired protection may be achieved in step 317 by providing a conformal covering (not shown) over the layers on the unexposed surfaces, such as an polymer conformal protective layer. In another preferred embodiment, the exposed surface may also be isolated from external thermal, mechanical, chemical, electrical, magnetic, or radiation damage by covering with a layer of ceramic or porous rigid material mesh. In yet another preferred embodiment, the exposed surface may be covered with a layer that enhances the selectivity of the feed species reaching the active surface. Such a layer can include, but is not limited to, polymers, metals, zeolites, self-assembled materials, or porous media, each of which has a higher permeability for the analyte of interest and a lower permeability for other species that are not of interest. In some preferred embodiments the exposed surface is covered with polymers such as but not limiting to polyethylene, polypropylene, teflon, polycarbonates, or polyaromatics. However, it is generally preferable that any covering on the exposed surface does not impede the interaction of the analyte or analytes to be transformed with the active layer by an amount greater than the species that are not of interest. Exceptions to this general rule may be made in certain cases, for example, when it is critical to protect the element from destructive effects of the environment. In another embodiment, steps 317 and 319 may be skipped.

FIG. 4 shows an exemplary chemical transformation system or reactor 400 in using the chemical transformation processes and devices in accordance with the present invention. The reactor 400 shown in FIG. 4 is notable for its simplicity due to the fact that high pressures and high temperatures are not required because of the superior performance of transformation device 401 in accordance with the present invention. The electrodes of device 401 are coupled in a circuit with power supply 402 so as to supply an electromagnetic field between the opposing electrodes of device 401. The circuit shown in FIG. 4 is illustrative; it may be replaced with any suitable circuit that can provide a flow of charge, internally (such as but not limiting to ohmic or ion flow or hole flow based current) or externally (such as but not limiting to eddy current or induced current from applied electromagnetic field) or both, in a given application.

Power supply 402 may supply direct current, alternating current, or any other form of electromagnetic waveform. The charge may be induced to flow in the device when the device is wired or through the use of wireless techniques.

The device 401 may include a single device such as shown in FIG. 1B and FIG. 2 or an array of elements such as shown in FIG. 1B and FIG. 2. The electrodes of the device(s) 401 may alternatively provide means to connect the device to induce interaction with an externally induced field such as but not limited to radio frequency or microwave frequency waves, or the equivalent.

Reactor 400 includes an inlet port 403 for receiving a feed stream and an outlet 404 producing a reactant stream. In operation, feed gas or liquid passes in contact with device 401 while power supply 402 is active and is transformed before passing from outlet 404. Device 401 shown in FIG. 4 may be placed in reactor 400 in various ways to manufacture and practice useful equipment such as, but not limiting to, obtrusive or non-obtrusive manner, as randomly or periodically arranged packed bed, with or without baffles to prevent short circuiting of feed, in open or closed reactors, inside pipes or separately designed unit, with accessories such as mixers, in a system that favors laminar or plug or turbulent or no flow, sealed or unsealed, isolated or non-isolated, heated or cooled, pressurized or evacuated, isothermal or non-isothermal, adiabatic or non-adiabatic, metal or plastic reactor, straight flow or recycle reactor, co-axial or counter-axial flow, and reactor or array of reactors that is/are available.

Table 3 lists example reactor technologies that may be used in accordance with the present invention. To illustrate the scope without limiting it, some examples from the art are listed in Table 3 and some in Kirk-Othmer Encyclopedia of Chemical Technology, Reactor Technology, John Wiley & Sons, Vol 20, pp 1007–1059 (1993) which is hereby incorporated by reference.

TABLE 3

Illustrative reactor designs

| | | |
|---|---|---|
| Stirred Tank | Tubular | Tower |
| Fluidized Bed | Batch | Continuous |
| Packed Bed | Film | Recycle |
| Plug Flow | Semibatch | Non-ideal |
| Membrane | Bioreactor | Multistage |

In another preferred embodiment, the catalyst is activated by passing current through the catalyst which results from applying an electrical voltage drop across the catalyst material. The catalyst is heated to a temperature greater than 500° C., preferably greater than 1000° C., most preferably greater than 1500° C. The heating of the catalyst can be achieved by conducting an exothermic reaction as well in combination or without the electrical current passing through the material. A non-limiting illustration of exothermic reaction is combustion of hydrocarbons.

The hot catalyst is then quenched rapidly by the removal of the applied current. The quenching can also be accomplished by contacting to the hot catalyst a cold gas such as that derived from liquid nitrogen, liquid argon or any other fluid. Rapid quenching reduces secondary reactions that may otherwise reduce yield or produce unwanted species. It is preferred that the quenching medium contains some or all of the species which would form the reactants after the activation of the catalyst. The activated catalyst so produced by in-situ thermal quench techniques may then be used in catalytic processes such as but not limiting to the various embodiments taught in this specification.

The ohmic or exothermic reactions may lead to thermal runaway. Thermal runaway refers to an situation in which the processes supplying heat to the reaction sites of the catalyst produce heat at a faster rate than can dissipate from the site. While thermal runaway is normally considered to be a problem, for this embodiment thermal runaway offers a surprising opportunity to reach very high temperatures and large quenching. The thermal runaway may be controllably induced in accordance with the present invention by applied electromagnetic field with or without the presence of exothermic reactions during the activation process. So long as the heat generated by the exothermic reactions is by itself insufficient to cause a self-sustaining thermal runaway, the thermal runaway can be controlled by application of the electromagnetic field.

Applications

The method and techniques disclosed can be applied to prepare catalysts and devices in manufacturing of useful chemicals and drugs. The superior performance of the method and device proposed for chemical composition transformation may be used to produce intermediates or final products. Some illustrative, but not limiting reaction paths where this invention can be applied are listed in Table 4. Reactions that utilize one or more elementary reaction paths in Table 4 can also benefit from the teachings herein. The benefits of such applications of teachings are many. To illustrate but not limit, the near ambient condition operation can reduce the cost and ease the ability to control chemical synthesis; it can in some cases lesser levels of thermal shocks during start ups and shut downs can enhance the robustness of the catalysts. In general the invention can be applied to produce useful materials from less value added materials, readily available raw materials, or waste streams.

TABLE 4

| | | |
|---|---|---|
| A + s ⟷ As | 2A + s ⟷ $A_2$s | A + 2s ⟷ $2A_{1/2}$s |
| As ⟷ Rs | $A_2$s + s ⟷ 2As | $2A_{1/2}$s ⟷ Rs + s |
| Rs ⟷ R + s | As ⟷ Rs | Rs ⟷ R + s |
| | Rs ⟷ R + s | |
| A + s ⟷ As | A + s ⟷ As | A + s ⟷ As |
| As + s ⟷ Rs + Ss | As ⟷ Rs + S | B + s ⟷ Bs |
| Rs ⟷ R + s | Rs ⟷ R + s | As + Bs ⟷ Rs + s |
| Ss ⟷ S + s | | Rs ⟷ R + s |
| A + s ⟷ As | A + 2s ⟷ $2A_{1/2}$s | B + s ⟷ Bs |
| B + s ⟷ Bs | B + s ⟷ Bs | A + Bs ⟷ Rs + S |
| As + Bs ⟷ Rs + Ss | $2A_{1/2}$s + Bs ⟷ Rs + Ss + s | Rs ⟷ R + s |
| Rs ⟷ R + s | Rs ⟷ R + s | |
| Ss ⟷ S + s | Ss ⟷ S + s | |

One of the significant commercially important application of this invention is in providing candidates to and in improving the performance of catalysis science and technology. This is particularly desirable for existing precious-metal and non-precious metal based catalytic formulations, heterogeneous and homogeneous catalysis, and for catalytic applications such as but not limiting to those and as known in the art and which are herewith included by reference. To illustrate the scope without limiting it, some examples where this invention can be applied are listed in Tables 5A, 5B, 5C, 5D, 5E, 5F and some are listed in the art such as Kirk-Othmer Encyclopedia of Chemical Technology, Catalysis, John Wiley & Sons, Vol 5, pp 320–460 (1993) and references contained therein.

TABLE 5A

ILLUSTRATIVE APPLICATIONS

| Catalyst | Reaction |
|---|---|
| metals (e.g., Ni, Pd, Pt, as powders or on supports) or metal oxides (e.g., $Cr_2O_3$) | C=C bond hydrogenation (e.g., olefin + $H_2$ • paraffin) |
| metals (e.g., Cu, Ni, Pt) | C=O bond hydrogenation (e.g., acetone + $H_2$ • 2-propanol) |
| metal (e.g., Pd, Pt) | Complete oxidation of hydrocarbons, oxidation of CO |
| Fe, Ru (supported and promoted with alkali metals) | 3 $H_2$ + $N_2$ → 2 $NH_3$ |
| Ni | CO + 3 $H_2$ → $CH_4$ + $H_2O$ (methanation) |
| | $CH_4$ + $H_2O$ → 3 $H_2$ + CO (steam reforming) |
| Fe or Co (supported and promoted with alkali metals) | CO + $H_2$ • paraffins + olefins + $H_2O$ + $CO_2$ (+ oxygen-containing organic compounds) (Fischer-Tropsch reaction) |
| Cu (supported on ZnO, with other components, e.g., $Al_2O_3$) | CO + 2 $H_2$ → $CH_3OH$ |
| Re + Pt (supported on $Al_2O_3$ and promoted with chloride) | paraffin dehydrogenation, isomerization and dehydrocyclization (e.g., heptane → toluene + 4 $H_2$ ) (naphtha reforming) |

TABLE 5A-continued

ILLUSTRATIVE APPLICATIONS

| Catalyst | Reaction |
|---|---|
| solid acids (e.g., $SiO_2$—$Al_2O_3$, zeolites) | paraffin cracking and isomerization; aromatic alkylation; polymerization of olefins |
| $Al_2O_3$ | alcohol → olefin + $H_2O$ |
| Pd supported on zeolite | paraffin hydrocracking |
| metal-oxide-supported complexes of Cr, Ti, or Zr | olefin polymerization (e.g., ethylene • polyethylene) |
| metal-oxide-supported complexes of W or Re | olefin metathesis (e.g., 2 propylene • ethylene + butene) |
| $V_2O_5$ or Pt | $2\ SO_2 + O_2 \to 2\ SO_3$ |
| $V_2O_5$ (on metal-oxide support) | naphthalene + 9/2 $O_2$ → phthalic anhydride + 2 $CO_2$ + 2 $H_2O$ <br> oxylene + 3 $O_2$ → phthalic anhydride + 3 $H_2O$ |
| Ag (on inert support, promoted by alkali metals) | Ethylene + ½ $O_2$ → ethylene oxide (with $CO_2$ + $H_2O$) |
| bismuth molybdate, uranium antimonate, other mixed metal oxides | propylene + ½ $O_2$ • acrolein <br> propylene + 3/2 $O_2$ + $NH_3$ • acrylonitrile + 3 $H_2O$ |
| mixed oxides of Fe and Mo | $CH_3OH + O_2$ • formaldehyde (with $CO_2$ and $H_2O$) |
| Fe3O4 or metal sulfides | $H_2O + CO$ • $H_2 + CO_2$ (water gas shift reaction) |
| Co—Mo/$Al_2O_3$ (S) and Ni—Mo/$Al_2O_3$ (S) and Ni—W/$Al_2O_3$ (S) | olefin hydrogenation, aromatic hydrogenation hydrodesulfurization, hydrodenitrogenation |

TABLE 5B

ILLUSTRATIVE APPLICATIONS

| Catalyst | Industry process |
|---|---|
|  | Hydrogen, carbon monoxide, methanol, and ammonia |
| ZnO, activated C supported Ni, Cr-promoted Fe | Feed pretreatment for reforming |
|  | Reforming |
| CuO—ZnO—$Al_2O_3$ | Shift reaction |
| supported Ni | Methanation |
| promoted Fe | Ammonia synthesis |
| Cu—Cr—Zn oxide, Zn chromite | Methanol synthesis |
|  | Hydrogenation |
| 25% Ni in oil | Edible and inedible oil |
| activated Ni | Various products |
|  | Dehydrogenation |
| chrome alumina | Butadiene from butane |
| promoted Fe oxide | Styrene from ethylbenzene |
|  | Oxidation, ammoxidation, oxychlorination |
| supported Ag | Ethylene oxidedrom ethylene |
| Pt—Rh gauze | Nitric acid from ammonia |
| $V_2O_5$ on silica | Sulfuric acid from sulfur dioxide |
| $V_2O_5$ | Maleic anhydride from benzene |
| $V_2O_5$ | Phthalic anhydride from o-xylene and naphthalene |
| copper chloride | Ethylene dichloride |
|  | Organic synthesis |
| Pt and Pd on C and $Al_2O_3$ | petrochemicals and specialty chemicals |

TABLE 5B-continued

ILLUSTRATIVE APPLICATIONS

| Catalyst | Industry process |
|---|---|
| anhydrous $AlCl_3$ | Ethylbenzene, detergent alkylate, etc. |
| phosphoric acid | Cumene, propylene trimer, etc. |
|  | Polymerization |
| Al alkyls and/or $TiCl_3$ | Ziegler-Natta processing |
| Cr oxide on silica | Polyethylene (by Phillips process) |
| Peresters | Polyethylene (low density) |
| Percarbonates | Poly (vinyl chloride) |
| benzoyl peroxide | Polystyrene |
| Amines, organotin compounds | Polyurethanes |

TABLE 5C

ILLUSTRATIVE APPLICATIONS

Oxychlorination Catalysts (Fixed bed/Fluid bed)
Catalysts for Methyl Chloride, Methyl Amine, and Melamine processing
Catalysts for isomerization of low carbon hydrocarbons such as C4 and C5/C6
Guard bed catalyst
HDS, HDN, hydrodemetallization and hydrogenation catalyst
Metal and Alloy Catalysts such as but not limiting to NiMo and CoMo
Sulfided catalyst
Catalysts for Ethylene Oxide (EO), one of the major building blocks of the chemical industry, used in the manufacture of Mono Ethylene Glycol (MEG), Ethoxylates, Ethanolamines and many other derivatives. MEG itself is a feedstock for the production of antifreeze, polyester, fibers and PET bottles.
Catalysts for $CO_2$ Lasers and other equipment so that they can be operated without replenishing the operating gases
Sponge Metal catalysts (also known as raney catalysts)

TABLE 5D

ILLUSTRATIVE APPLICATIONS

Catalysts for FCC Pretreatment
Catalysts for hydrotreatment of heavy VGO or VGO/Resid blends with a high metals content, high CCR and high final boiling point.
Catalysts for Hydrocracking Pretreatment, Mild Cracking, and Hydrocracking
Hydroprocessing catalysts and Fluid Cat Cracking (FCC) Catalyst
Pretreat catalysts in general, such as but not limiting to hydrodemetallization, Conradson carbon removal, hydrodenitrogenation and hydrodesulfurization.
Amorphous and zeolite based Hydrocracking catalysts.
Catalysts for Resid hydrotreatment
Catalysts to derive maximum product value from LPG olefins such as propylene, iso-butylene and iso-amylenes.
Catalysts to maximize octane barrels by improving octane without sacrificing gasoline yield.
Catalysts to maximize production of transportation fuels such as gasoline and diesel from any feedstock.
Catalysts for maximum mid-distillate production, such as diesel and jet fuels.
Catalysts to extend the frontiers of resid cracking, balancing bottoms conversion, low delta coke and metals tolerance.
Catalysts for maximum octanes (RON and MON) and light olefins production

TABLE 5D-continued

ILLUSTRATIVE APPLICATIONS

Catalysts to provide maximum octane barrels for applications where excellent octanes at maximum gasoline yield is required

TABLE 5E

ILLUSTRATIVE APPLICATIONS

Catalysts for selective catalytic reduction (SCR) technology. Illustrative, but not exhaustive applications include Gas Turbines, Chemical Plants (e.g. Nitric Acid, Caprolactam, etc.), Waste Incinerators, Refinery Heaters, Ethylene Crackers, and Gas Motors.
Zeolites and related applications of zeolites (Adsorption, Separation, Catalysis, and Ion Exchange)
Emission-control coatings and systems that remove harmful pollutants, improve fuel economy and enhance product performance in a wide range of applications, including: trucks and buses, motorcycles, lawn and garden tools, forklifts, mining equipment, aircraft, power generation, and industrial process facilities.
Surface coatings for design, manufacture and reconditioning of critical components in aerospace, chemical and petrochemical industries.
Catalysts used in preparing, processing, and treating semiconductor industry gases, liquids, and emissions
Catalysts are capable of destroying ozone (the main component of smog) already in the air.
Catalysts to lower ozone, NOx, and SOx levels
Catalysts for Combustion
Catalysts to improve air quality

TABLE 5F

ILLUSTRATIVE APPLICATIONS OF CLAIMED INVENTION

Catalysts that facilitate the manufacture of petrochemicals, fine chemicals, fats, oils and pharmaceuticals and aid in petroleum refining.
Catalysts that purify fuel, lubrication oils, vegetable oils and fats.
Catalysts for water filtration technologies.
Food and Beverage Industry Catalysts.
Paper, Pulp, and Glass Industry Catalysts
Catalysts for producing Inorganic chemicals
Antimicrobial Catalysts
Catalysts to in-situ produce chemicals used in households
Enzyme and Microbial Catalysts
Catalysts used in biomedical business. Important products include but do not limit to powerful narcotic-based pain killers such as sufentanil, fentanyl base and hydromorphone.
Catalysts used in forensic equipment and sensors
Catalysts used in analytical instruments The teachings of the present invention can be used to research and develop, to rapidly screen novel catalysts by techniques such as combinatorial methods, and to optimize catalysts through the use of arrays in electrical and microelectronic circuits.

The application of electrical current in particular, and electromagnetic field in general, can enable the ability to extend the life of catalysts, or improve their activity, yields, light off temperatures, turn over rates, stability, and selectivity with or without simultaneous changes in the operating conditions such as temperature, pressure, and flow profile. The catalyst so operated with electromagnetic field is anticipated to enable reactor temperatures and pressures or conditions that are more desirable to customers and integrated to the operating conditions of a specific manufacturing scheme. Furthermore, this invention of applying electromagnetic effects on the catalyst can enable reaction schemes that are switched on or off at will by switching on or off of the electromagnetic field respectively. Such flexibilities can be highly valuable in controlling and enhancing of safety of reactions that may be explosive or that may yield dangerous and hazardous byproducts. The invention can also be applied to produce multiple useful products from same reactor through the variation on-demand of the applied electromagnetic field or feed or other operating conditions required to meet the needs of a particular application.

The benefits of this invention can be practiced in lowering the light-off temperatures in combustion exhaust systems. As one illustration of many applications, it is known in the art that emission control catalysts such as the three-way catalysts placed in automobile exhausts operate efficiently at temperatures greater than about 350° C. These non-ambient temperatures require a heat source and often the exhaust heat from the vehicle's engine is the principal source of the needed heat. During initial start up phase of the engine, it takes about a minute to heat the catalyst to such temperatures. Consequently, the vehicle emission controls are least effective during the start. Methods to rapidly heat the catalyst to such temperatures or lower temperature catalysts are desired. Methods have been proposed to preheat the catalysts by various techniques, however, such techniques require high power to operate, add weight, and are not robust. The teachings contained herein can be used to prepare catalytic units or modify existing catalytic units to operate at lower temperatures (less than 350° C., preferably less than 200° C.) and quicker light-offs. These teachings apply to combustion in general and to emission control systems used in other mobile and stationary units. The teachings may also be practiced by coating the engine cylinder's inside, operating the said coating with electrical current during part of or the complete combustion cycles. Such an approach can help modify the reaction paths inside the cylinder and thereby prevent or reduce pollution-at-source.

The benefits of the teachings contained herein can be applied to the control of difficult-to-treat species such as NOx, SOx, CFCs, HFCs, and ozone. One method is to prevent these species from forming through the use of novel catalytic devices with electrical current in particular, and electromagnetic field in general. Alternatively, using such catalytic devices with electrical current, streams containing these species may be treated with or without secondary reactants such as CO, hydrocarbons, oxygen, ammonia, urea, or any other available raw material, or combinations thereof.

The invention is particularly useful for applications that currently require high temperatures or heavy equipment due to inherently high pressures during reaction or excessive volumes, as the teachings of the presently claimed invention can offer a more economically desirable alternative. Illustrations of such applications, without limiting the scope of this invention, include pollutant treatment or synthesis of fuel and useful chemicals in space vehicles, submarines, fuel cells, miniature systems in weight sensitive units such as automobiles, airplanes, ships, ocean platforms, remote sites and habitats. This can help reduce the weight of the unit, reduce capital costs, reduce inventory costs, and reduce operating costs. Any applications that desire such benefits in general can utilize the teachings of this invention.

The invention can offer a long sought alternative for catalyzing reactions on feeds that contain poisoning species, i.e. species that can cause reversible or irreversible poisoning of available catalysts (for example, but not limiting to, illustrations in Table 6A and 6B).

TABLE 6A

| Process or Product | Catalytic Material | Catalyst Poisons |
|---|---|---|
| Ammonia | FeO/Fe$_2$O$_3$ promoted by Al$_2$O$_3$ and K$_2$O | Moisture, CO, CO$_2$, O$_2$, compounds of S, P, and As |
| Aniline | Ni powder, Al$_2$O$_3$ Raney-Ni or -Cu, Cu- chromite | Groups VA and VIA elements |
| Butadiene | Ca$_8$Ni(PO$_4$)$_6$ Cr$_2$O$_3$ on Al$_2$O$_3$ Bi-molybdate Fe$_2$O$_3$ + Cr$_2$O$_3$ + K$_2$O | Halides, O$_2$, S, P, Si |
| Ethanol | H$_3$PO$_4$ on Kieselguhr | NH$_3$, O$_2$, S, organic base |
| Ethylene oxide | Ag-oxide on refractory oxide | Compounds of S |
| Formaldehyde | Ag on Al$_2$O$_3$ Ag needles FeO$_3$ +MoO$_3$ | Cl$_2$, S compounds |
| Methanol | ZnO + Cr$_2$O$_3$ CuO | S compounds, Fe, Ni S compounds |
| Nitric acid | Pt on Rh | Compounds of As and Cl$_2$ |
| Polyethylene | Al-alkyl-Ti tetrachloride Precipitate | Moisture, alcohols, O$_2$, So$_2$, COS, CO$_2$, Co |
| Styrene | (a) Fe$_2$O$_3$ + K$_2$O + Cr$_2$O$_3$ (b) Fe$_2$O$_3$ + K$_2$CO$_3$ + Cr$_2$O$_3$ + V$_2$O$_5$ | Halides, S compounds, O, P, Si |
| Sulfuric Acid | V$_2$O$_5$ + K$_2$O on Kieselguhr | Halides, As, Te |
| Cracking, alkylation, and isomerization of petroleum fraction | Synthetic aluminosilicate; AICl$_3$ H$_3$PO$_4$ | Organometallic compounds, organic bases |
| Desulfurization, denitrogenation, and deoxygenation | (NiO + MoO$_3$) (CoO + MoO$_3$) or (NiO + WO$_3$) on alumina | H$_2$S, CO, CO$_2$, heavy hydrocarbon deposits, compounds of Na, As, Pb |

TABLE 6B

| Reaction | Active catalyst | Poisons and inhibitors | Mode of action |
|---|---|---|---|
| NH$_3$ synthesis | Fe | S, Se, Te, P, As compounds, halogens O$_2$, H$_2$O, NO CO$_2$ CO unsaturated hydrocarbons | poison: strong chemisorption or compound formation weak poison: oxidation of Fe surface: reduction possible, but causes sintering inhibitor: reaction with alkaline promoters poison and inhibitor: strong chemisorption, on reduction slowly converted to methane: accelerates sintering inhibitor: strong chemisorption, slow reduction |
| Hydrogenation | Ni, Pt, Pd, Cu | S, Se, Te, P, As compounds, halogens Hg and Pb compounds | poison: strong chemisorption poison: alloy formation poison: surface |
| Catalytic cracking | alumino-silicate | O$_2$ CO amines, H$_2$O coking | oxide film Ni forms volatile carbonyls inhibitor: blockage of active centers poison: blockage of active centers |
| NH$_3$ oxidation | Pt—Rh | P, As, Sb, compounds; Pb, zn, Cd, Bi rust alkaline oxides | poison: alloying, gauze becomes brittle causes NH$_3$ decomposition poison: reacts with Rh$_2$O$_3$ |
| SO$_2$ oxidation | V$_2$O$_5$—K$_2$S$_2$O$_7$ | As compounds | inhibitor • poison: compound formation |

To illustrate this feature of the present invention, it is well known in the art that precious metal catalysts are useful in numerous reactions. However, these and other catalysts tend to get poisoned when the feed stream contains sulfur or sulfur containing species. Extensive and often expensive pre-treatment of the feed streams is often required to ensure that the catalyst is not poisoned. The present invention describes materials and devices that can catalyze reactions with non-precious metal based formulations that are not known to be poisoned by sulfur. Thus, through appropriate variations in catalyst composition and electromagnetic field, chemical reactions may be realized even if poisoning species are present. This reduces or eliminate the need for expensive and complex pre-treatment of feed streams.

This method is not limited to precious metal poisoning and can be applied to finding catalyst alternatives for presently used catalysts that are based on other materials (supported, unsupported, precipitated, impregnated, skeletal, zeolites, fused, molten, enzyme, metal coordination, ion exchange, bifunctional, basic, acidic, sulfide, salt, oxide, metal, alloys, and intermetallic catalysts). The method is also not limited to sulfur poisoning and the teachings can be used when poisoning or loss in stability is caused by species other than sulfur. The method can also be applied to cases where solutions need to be found for catalysts or systems that undergo coking, thermal run away, and chemical effects.

The invention also offers a method of developing and practicing non-precious alternatives to expensive precious metal-based catalysts. This can reduce catalyst costs. Such uses of invention are desirable in automobile exhaust catalysts, emissions treatment catalysts, naphtha catalysts, petroleum cracking catalysts, and applications that utilize precious metals. Notwithstanding such use and uses discussed earlier, these teachings are not meant to limit to the teachings of presently claimed invention to non-precious metals and materials based thereof. Precious metals and materials based thereof may be used in the practice of this invention's teachings.

The benefits of this invention may be obtained where localized heating is desired because, at contact points between the catalytic particles, the grain boundaries may be hot because of the ohmic heating. These localized hot spots can offer active sites for chemical reactions. Given the nanostructured form of the catalysts, these microscopic hot spots are localized because of the low thermal conductivity of the porous ceramic substrate. Such localized heating would raise the reaction temperatures very locally, i.e. only of gas molecules that are in immediate vicinity or in direct contact with the catalyst. Once the products leave the hot spot, the product compositions are expected to quench from thermal collisions and low bulk temperatures. Hence, the present invention enables thermally activated reactions to be confined to the vicinity of the catalyst.

Such a localized heating phenomena may dramatically limit the secondary series reactions. In conventional catalysts that are heated by external furnace, both the active site temperatures and the bulk gas temperatures are high. Therefore, in conventional catalysis, the products can participate in secondary series reactions leading to complex reaction pathway and possibly poor selectivity. When raw materials are preheated, for example, reactions may occur before contact with the catalyst. When the reaction environment itself is heated, secondary reactions may continue after contact with the catalyst. These secondary reactions are independent the desired catalytic reactions and so may produce undesirable effects and/or products.

In electrically activated catalysis in accordance with the present invention, an unusual flexibility exists as it can provide localized hot spots suitable for selective chemistry that is dependent on (i.e., assisted by) the catalyst, and then low bulk temperatures before and after catalyst contact suitable for limiting the kinetics of secondary reactions. These benefits are anticipated when the grain surface is similarly or more or less conductive than the grain bulk. In other words, one of the unique inventions disclosed here is the method of conducting useful chemical reactions and transformations from any raw material when the active site on the catalyst surface is heated by the flow of current while the bulk of the reactor environment is maintained at a different temperature (difference is preferably greater than 10° C.). It is important to note that for the described benefit, the substrate on which the catalyst is deposited should offer higher impedance to current than the catalyst itself, and preferably the impedance of the substrate should be 50% or more than the impedance of the catalyst.

Most and preferably substantially all the current flows in the catalyst rather than the catalytic support. It is known to use current flowing in the catalytic support to create ohmic heating that modifies the catalytic performance and/or regenerates the catalyst affixed to the support. However, the present invention operates to cause current in the catalyst, and is not concerned primarily with heating or current flow in the catalytic support structure. Preferably, current flowing in the catalyst exceeds the current flowing through the catalytic support. More specifically, for example, current flowing in the catalyst represents more than 75%, more preferably more than 90%, and still more preferably greater than 95% of the total available current. This can be implemented, for example, by using insulating, semi-insulating, and/or highly resistive materials and structures to support the catalyst.

The benefits of this invention may also be applied in the design of novel catalysts and other performance materials. Catalytic activity has its origin in the electronic state of a substance (i.e. amongst other things the number of electrons and the orbitals associated with these electrons). It is known that precious metals (Pt, Pd, Ir, Ru, etc.) show superior catalytic activity for a wide range of chemical reactions. However, these elements are expensive. There has been a need for a technology that can help design substance that are more affordable than precious metals and yet that show performance comparable with the precious metals.

An embodiment of the present invention involves modification of the electronic state of a substance through the application of an electromagnetic field applied to the substance. The application of an electromagnetic field may be used to modify the performance of such materials (e.g. catalytic, structural, thermal, electromagnetic, optical, photonic, physical, chemical, biological performance). This may be achieved by the application of an electrical field (such as passage of current or application of a voltage gradient) or through induced field. While the former method is explained in detail elsewhere in this disclosure, the later method is illustrated hereinafter.

It is known to those in the art that dissimilar substances in contact induce an electromagnetic potential. This effect is in part the basis of Seebeck and Peltier Effects. This induced voltage offers another opportunity to modify the electronic state of a substance and consequently modify the materials performance. For example, a combination of disparate nanostructured particles can be formed by any available mixing technique such that particles with different compositions are sufficiently adjacent that the share domain boundaries. In other words, their domain boundaries overlap. Because their domain boundaries overlap, it is believed that an electromagnetic field is induced about the domain boundary. This induced electromagnetic field, either alone or in combination with an externally applied electromagnetic field, modifies the catalytic performance of the combined nanostructured materials.

This effect is believed to be more pronounced in dissimilar materials when these materials are in nanostructured form. This is believed to be because of the fact that nanostructured materials have high interface area. This provides more interaction of the surface atoms of the contacting substances. With particle sizes smaller than the critical domain sizes of the materials involved, these effects are believe to be more pronounced. With very small clusters, this effect is expected to be most pronounced. In this embodiment, two or more dissimilar nanomaterials are formed into a structure where the dissimilar nanomaterials share grain boundaries. At the grain boundaries, the dissimilarity induces an electromagnetic potential in the grains, i.e. one grain is somewhat positively induced and the other is negatively induced. The charge so induced affects the Fermi level electrons in the respective material. Given the fact that the useful performance and properties of a material are in part dependent on the nature and state of the Fermi electrons in a material, induced charge in a material is anticipated to modify the performance of the material by 5% or more.

These effects can be used to generalize a method of making useful catalytic materials from nanomaterials. This embodiment involves a method of manufacturing catalysts with nanomaterials where two or more dissimilar materials are formed into a structure such that at least at some of the grain boundaries there is interaction between the dissimilar materials. Furthermore at these grain boundaries there is an induced charge in the nanostructured grains because of the dissimilar material compositions. This induced charge modifies the performance of the material in contrast to the state where the material has no induced charge. Such dissimilar nanomaterial catalysts may be used to conduct useful chemical reactions and transformations from any raw material. Furthermore, nanomaterial structures of these types may be used to modify other performance of the material as well in other applications, e.g. structural, thermal, electromagnetic, optical, photonic, physical, chemical, biological. Finally, one may use a dielectric, ferromagnetic, or other materials to allow one to combine external electromagnetic field and the induced charges for beneficial modification of the materials' performance.

It should be noted that these embodiments are akin to, yet distinct from, alloy catalysts. For example, this embodiment of the invention requires the use of materials in a form that has high interfacial area per unit volume. Furthermore, it is necessary in this embodiment that electromagnetic interactions occur between the different materials at these interfacial grain boundaries. In contrast, in alloyed mixtures there are no grain boundaries and there is no electromagnetic interaction between the different constituent of an alloy. Also, there are a limited set of materials that will form alloys, and the materials structures of the present invention include a much wider range of materials including materials that normally cannot be alloyed together.

Similarly, it should be noted that this embodiment is akin to, yet distinct from, catalysts that are produced by mixing different materials (metals, oxides, alloys, etc.). As stated above, this embodiment of the invention requires the use of materials in a form that has high specific interfacial area. Furthermore, it is necessary in this embodiment that electromagnetic interactions occur between the different materials at these interfacial grain boundaries. In contrast, in catalyst produced by mixing materials, other than grain contact leading to point junctions, there is no intimate contact between the mixed materials. Furthermore, the mixed materials are essentially equipotential with no electromagnetic interaction between the different constituent of the mixture. The embodiment explained here requires that there be an interaction and that the nanomaterials interfaces be not at the same electromagnetic potential.

As specific example of implementing an embodiment of induced voltage, when cobalt nanomaterial and gold nanomaterial are mixed, it is anticipated that cobalt will perform with a nickel-like behavior while gold will perform with a platinum-like behavior (because platinum is next to gold in the periodic table and gold Fermi electrons under induced charge are expected to behave like platinum Fermi electrons; similarly nickel is next to cobalt in the periodic table and cobalt Fermi electrons under induced charge are expected to behave like nickel Fermi electrons) . As another example, when iron and silver nanoparticles are mixed, it is anticipated that cobalt-like and palladium-like behavior will be observed. As yet another example, when tungsten and gold nanoparticles or nanofilms are brought into proximity, rhenium and platinum-like performance is anticipated to be observed at the interface and interface influenced sites. Also, a mixture of tantalum and copper nanoscale clusters is expected to yield a tungsten and nickel-like performance. This behavior is expected to be observed even in non-stoichiometric substances, e.g. non-stoichiometric reduced mixtures of metal oxides, nitrides, carbides, borides, oxonitrides, carbonitrides, and other substances. While the above illustrates the embodiment with two metals, these teachings can be applied to more than two metals and to substances that are not metals.

While this disclosure specifically teaches methods and processes for engineering catalytic performance of substances through the use of applied or induced charge, the teachings can be applied in general to engineer the structural, thermal, electrical, magnetic, electronic, optical, photonic, electrochemical, physical, chemical, biological performance of substances as well, through the application of applied or induced charge. Such engineering using induced or applied charge is expected to yield performance enhancements greater than 5% over the case where no charge is induced or applied. Both applied and induced electromagnetic potential may be utilized for engineering the performance of a substance or mixture of substances.

The benefits of this invention may also be applied where the charge flow through the catalyst affects the surface potential of active sites. It may also participate in the surface diffusion of any radicals or charged species adsorbed on the catalyst's surface. In such a case, the charge flow can be responsible in modifying the adsorption and desorption kinetics of the species involved in the chemical reaction. The surface charge potential can also have some steric influences. These effects can be pronounced if the rate limiting step in a specific chemistry is either surface diffusion or the adsorption/desorption of specific radicals on the surface of the catalyst. Furthermore, this effect can be pronounced when the charge flow is primarily over the grain boundaries and surface of the catalyst. Electrical current, in such circumstances, can offer an additional independent process variable. This variable can help control a chemical pathway through variations in the applied and/or induced electromagnetic potential.

The benefits of the teachings contained in this invention can be utilized in research and development and manufacture of inorganic, organic, and pharmaceutical substances from various precursors, such as but not limiting to illustrations in Table 7A, 7B, 7C, 7D, 7E, 7F, and 7G(these and others can be found in literature).

TABLE 7A

Illustrative Inorganic Reactants and Product Candidate for Catalysis

| | | |
|---|---|---|
| Ammonia | Magnetite | Calcium carbide |
| Ammonium nitrate | Oxides | Calcium carbonate |
| Ammonium carbonate | Nitric acid | Calcium chloride |
| Ammonium perchlorate | Phosphoric acid | Calcium cyanamide |
| Ammonium sulfite | Nitrogen oxides | Calcium hydroxide |
| Carbon | Metals and Alloys | Sulfur |
| Carbon dioxide | Pyrite | Thiourea |
| Carbon disulfide | Sulfur Oxides | Titanium dioxide |
| Carbon monoxide | Carbonates | Urea |
| Radicals | Sodium nitrate | Zinc sulfide |
| Lead Sulfide | Sodium sulfite | Sulfur dioxide |
| Ozone | Alkalis | Hydrogen Sulfide |

TABLE 7B

Illustrative Inorganic Reactions Candidate for Application of this Invention

| Reaction | Current Catalyst |
|---|---|
| Para-$H_2$ conversion | hydrated Fe oxides |
| Production of $H_2$ and CO steam reforming of methane $H_2O + CH_4 \rightarrow 3H_2 + CO$ | Ni/$Al_2O_3$ |
| watergas shift reaction $CO + H_2O \rightarrow H_2 + CO_2$ | Fe—Cr oxides Cu—Zn oxides |
| Methanation $CO + 3 H_2 \rightarrow CH_4 + H_2O$ | Ni |
| Oxidation of $NH_3$ to NO $NH_3 + 1.25 O_2 \rightarrow NO + 1.5 H_2O$ | Pt—Rh wire gauze |
| Synthesis of amonia $N_2 + 3 H_2 \rightarrow 2 NH_3$ | $Fe_3O_4$ promoted With K, Ca, Mg, Al |
| Oxidation of $SO_2$ to $SO_3$ | $V_2O_5$ |
| Claus process recovery of S from $SO_2$ + $H_2S$ $2 H_2S + SO_2 \rightarrow 3 S + 2 H_2O$ | $Al_2O_3$ |
| Decomposition of $NH_3$ $2 NH_3 \rightarrow N_2 + 3 H_2$ | Ni/ceramic |

TABLE 7C

Organic Reactants and Product Candidate for Catalysis

| | | | |
|---|---|---|---|
| Acetaldehyde | Cyclohexane | Isobutene | Peracetic acid |
| Acetone | Metalorganics | Isocyanates, alcohols | Styrene |
| Acetylene | Cyclohexene | Isoprene | Propylene |
| Acrylonitrile | Cyclopentene | Methane | Adipic Acid |
| Amide | Ethane | Methanol | Aliphatics |
| Aliphatic glycols | Ethanol | Methyl methacrylate | Tetrachlorobenzene |
| Aniline | Ethyl acetate | Nitroacetanilide | Tetranitromethane |
| Acetic Acid | Ethyl nitrate | Nitroalkanes | Triphenylsilane |
| Alkanes | Ethyl nitrite | Nitrobenzene | Urea |
| Benzaldehyde | Ethylene | Aromatics | Alkenes |
| Benzene | Ethylene | 2,4-Dinitroacetanilide | Vinyl chloride |
| Ethyl nitrate | Butadiene | n-Pentane | Alkynes |
| Ethyl nitrite | m-Chloroaniline | Phenol, m-cresol | Dendrimers |
| Propylene | Propane | Propionic Acid | Ethylene Oxide |
| Aldehydes | Alcohols | Ketones | Acids |
| Anhydrides | Amines | Isomers | Oxides |
| Sulfur Organics | Phospho-Organics | Salts | Alkaloids |
| Styrene | Nitro Organics | Fullerenes | Bio-derived |
| Cumene | CFCs | HFCs | Monomers |
| Cycloalkanes | Cycloalkenes | Cycloalkynes | Cage Compounds |

TABLE 7D

Illustrative Organic Reactions Candidate for Application of the present Invention

| Reaction | Current Catalyst |
|---|---|
| Selective hydrogenation | |
| edible oils | Raney Ni, Ni—NiO/support |
| inedible oils | Raney Ni, Ni—NiO/support |
| acetylene → ethylene | supported Pd + Pb, S, quinoline |
| diolefins → olefins | Pd/Al$_2$O$_3$ |
| unsaturated aldehydes → saturated aldehydes | Pt/support |
| unsaturated aldehydes → saturated alchohols | Pt/support (Zn—Fe) |
| unsaturated nitriles → saturated nitriles | Pd/C |
| unsaturated anhydrides → saturated anhydrides | Pd/support |
| Aromatic hydrogenation | |
| benzene → cyclohexane | Ni/support, Raney Ni |
| phenol → cyclohexanone | Pt/support |
| phenol → cyclohexanol | Pt/Support or Ni |
| naphthalene → tetra- and decahydronaphthalenes | Ni/support |
| Asymmetric hydrogenation | Rh-cyclooctadiene with phosphine |
| Hydrogenation | |
| nitriles → amines | Raney Co |
| oximes → hydroxylamines | Pt or Pd |
| aldehydes → alcohols | NiO/support, Cu chromite |
| Reduction | |
| nitro compounds → amines | Pd/C, Cu chromite |
| acids → alcohols | Raney Co, Cu chromite |
| succinic anhydride → butyrolactone | Ni/SiO$_2$ |
| acyl chlorides → aldehydes (Rosenmund reaction) | Pd/BaSO$_4$ |

TABLE 7E

Illustrative Organic Reactions Candidate for Application of the present Invention

| Reaction | Current Catalyst |
|---|---|
| Dehydrogenation | |
| butenes → butadiene | Ca(Sr)Ni phosphate |
| ethylbenzene → styrene | Fe$_2$O$_3$—Cr$_2$O$_3$ (K$_2$O) |
| Butane → butadiene | Cr$_2$O$_3$/Al$_2$O$_3$ |
| Hexane → benzene | Pt/Al$_2$O$_3$ |
| Cyclohexane → benzene | Pt/Al$_2$O$_3$ |
| Cyclohexanol → cyclohexanone | ZnO (alkali) |
| Oxidative dehydrogenation | |
| butenes → butadiene | Bi molybdate |
| alcohols → aldehydes, ketones | ZnO, Cu chromite, Raney Ni |
| Liquid-phase oxidation | |
| ethylene → acetaldehyde | PdCl$_2$—CuCl$_2$ |
| propene → acetone | PdCl$_2$—CuCl$_2$ |
| butene → 2-butanone | PdCl$_2$—CuCl$_2$ |
| ethylene + acetic acid → vinyl acetate | PdCl$_2$—CuCl$_2$ |
| propene + acetic acid → allyl acetate | PdCl$_2$—CuCl$_2$ |
| cyclohexane → cyclohexanol + cyclohexanone | Co acetate |
| buane → acetic acid | Co acetate |
| actaldehyde → acetic anhydride | Co acetate |
| cylohexanol + cyclohexanone → adipic acid | V salt (+ HNO$_3$ as oxidant) |
| toluene → benzoic acid | Co acetate |
| benzoic acid → phenol | Cu |
| p-xylene → terephthalic acid | Co acetate |
| m-xylene → isophthalic acid | Co acetate |
| Vapor-phase oxidation | |
| ethylene → ethylene oxide | Ag/support |
| alcohols → aldehydes or ketones | Fe$_2$O$_3$—MoO$_3$ or Ag |
| propene, isobutene → unsaturated aldehydes | Cu$_2$O, Bi molybdate |
| o-xylene, naphthalene → phthalic anhydride | V$_2$O$_5$/TiO$_2$, V$_2$O$_5$—K$_2$S$_2$O$_7$/SiO$_2$ |
| butane or butene → maleic anhydride | V$_2$O$_5$—P$_2$O$_5$/support |
| benzene → maleic anhydride | V$_2$O$_5$—MoO$_3$, (P$_2$O$_5$)/support |

TABLE 7F

Illustrative Organic Reactions Candidate for Application of this Invention

| Reaction | Current Catalyst |
|---|---|
| Ammoxidation | |
| propene + NH$_3$ → acrylonitrile | Bi molybdate, U—Sb oxides |
| isobutene + NH$_3$ → methacrylonitrile | multicomponent oxide |
| toluene + NH$_3$ → benzonitrile | V$_2$O$_5$—MoO$_3$/Al$_2$O$_3$ |

TABLE 7F-continued

Illustrative Organic Reactions Candidate for Application of this Invention

| Reaction | Current Catalyst |
|---|---|
| m-xylene + $NH_3$ → isophthalonitrile | $V_2O_5$—$MoO_3$/$Al_2O_3$ |
| o-xylene +$NH_3$ → phthalonitrile | $V_2O_5$—$Sb_2O_5$ |
| 3- or 4-picoline + $NH_3$ → 3- or 4-cyanopyridine | $V_2O_5$—$MoO_3$/$Al_2O_3$ |
| methane + $NH_3$ → hydrogen cynanide | Pt—Rh wire gauze |
| Oxychlorination | |
| ethylene + 2 HCl + 0.5 $O_2$ → vinyl chloride + $H_2O$ | $CuCl_2$/$Al_2O_3$ |
| Hydration | |
| Ethylene → ethanol | $H_3PO_4$/$SiO_2$ |
| propene → 2-propanol | $H_3PO_4$/$SiO_2$ |
| Dehyrdation | |
| x-phenylethanol → styrene | $NaPO_3$/$SiO_2$, $Al_2O_3$ |
| higher alcohols → olefins | Zeolite |
| acids + ammonia → nitriles | $H_3PO_4$/$SiO_2$ |
| butylene glycol → butyrolactone | Zeolite |
| alcohols + ammonia → amines | $SiO_2$/$Al_2O_3$ |
| Miscellaneous reactions | |
| benzene + ethylene → ethylbenzene | $BF_3$/$Al_2O_3$, $AlCl_3$ |
| benzene + propene → cumene | $H_3PO_4$/$SiO_2$ |
| isocyanuric acid → melamine | $Al_2O_3$ |
| cumene hydroperoxide → phenol + acetone | $H_2SO4$ |

TABLE 7G

Illustrative Reactions Candidate for Application of this Invention

| Reaction | Current Catalyst |
|---|---|
| Methanol synthesis | $ZnO$—$Cr_2O_3$ |
| CO + 2$H_2$ → $CH_3OH$ | Cu—ZnO—$Al_2O_3$ |
| | Cu—ZnO—$Cr_2O_3$ |
| Methanation | |
| CO + 3 $H_2$ → $CH_4$ + $H_2O$ | Ni/$Al_2O_3$ |
| CO + $H_2$ → higher alcohols + $H_2O$ | $CuCoMo_{0.8}K_{0.1}$oxide, M = Cr, Mn, Fe, or V |
| Fischer-Tropsch synthesis | |
| CO + $H_2$ → hydrocarbons + $H_2O$ | Fe oxide (promoted) |
| Hydroformylation (Oxo reaction) | $HCo(CO)_4$ |
| olefin + CO + $H_2$ □ → aldehyde | $HRh(CO)(PPh_3)_3$ |
| Miscellaneous | |
| $CH_3I$ + CO → $CH_3COI$ | $[Rh(CO)_2I_2]$ |
| $CH_2O$ + $H_2$ + CO → $HOCH_2CHO$ | $HRh(CO)_2(PPh_3)_3$ |
| $CH_2O$ + CO + $H_2O$ → $HOCH_2COOH$ | Nafion-H resin |
| Addition | $RhCl_3$ |
| ethylene + butadiene → 1,4-hexadiene + 2,4-hexadiene | |
| Cyclization | |
| 2 butadiene → cis, cis-1,5-cyclooctadiene | $Ni(acrylonitrile)_2$ + $PPh_3$ |
| 3 butadiene → 2,5,9-cyclododecatriene | $Ni(acrylonitrile)_2$ |
| Olefin metathesis (dismutation) | Mo or W/$Al_2O_3$ or W/$SiO_2$ |
| 2 propene → ethylene + butene | |
| cyclohexene + ethylene → 1,7-octadiene | |

TABLE 7G-continued

Illustrative Reactions Candidate for Application of this Invention

| Reaction | Current Catalyst |
|---|---|
| Oligomerization | $Al(C_2H_5)_3$ |
| 2 ethylene → butene | |
| ethylene → $M_1$ -olefins | |
| Polymerization | |
| ethylene → polyethylene | $TiCl_4$ + $Al(C_2H_5)_3$ |
| propene → polypropylene (isotactic) | $CrO_3$/$SiO_2$ |
| | $MoO_3$/$Al_2O_3$ |
| butadiene → polybutadiene | $TiCl_3$ + $Al(C_2H_5)_3$ |
| 1,4-trans- | $Al(i-C_4H_9)_3$ + $VOCl_3$ |
| 1,4-cis- | $Al(i-C_4H_9)_2Cl$ + $CoCl_2$ |
| 1,2-isotactic | $Al(i-C_4H_9)_3$ + $Cr(PhCN)_6$ |
| 1,2-syndiotactic | $Al(i-C_4H_9)_3$ + $MoO_2(O-i-C_4H_9)_2$ |
| Petrochemistry | |
| Catalytic cracking | Zeolite, alumina-silica |
| Catalytic reforming | Pt/$Al_2O_3$ or bimetallic catal./$Al_2O_3$ |
| Alkylation | $H_2SO_4$ or HF |
| Isomerization | Pt/alumina |
| Hydrocracking | Ni/$SiO_2$—$Al_2O_3$ or Ni—W/$SiO_2$—$Al_2O_3$ or Pd/zeolite |
| Hydrofining or hydrotreating | Co—Mo/$Al_2O_3$, Ni—W/$Al_2O_3$ |

Application of the Present Invention

These benefits of the present invention can also be utilized in the manufacture of fuels, propellants, chemicals, biochemicals, petrochemicals and polymer. Furthermore, the use of electromagnetic energy and active materials in high surface area form can provide benefits in microbe-based, cell-based, tissue-based, and artificial implant-based devices and reaction paths. Finally, the benefits of this invention can be applied to gaseous, liquid, solid, superfluid, plasma or mixed phase reactions. These devices can be enabling to the production of improved and novel products. To illustrate, the catalyst with optimization techniques available in the art can enable devices to produce hydrogen from low cost chemicals, which in turn can be used to prepare hydrogen based engines, alternative fuel vehicles, hybrid vehicles, captive power generation and other applications.

To illustrate, the teachings contained herein, preferably combined with optimization techniques available in the art, can enable affordable devices to produce hydrogen from low-cost chemicals (such as but not limiting to methanol, agriculturally derived ethanol, gasoline, natural gas, gasohol), which in turn can be used to prepare hydrogen based engines, alternative fuel vehicles, hybrid vehicles, captive power generation and other applications. The teachings can assist in reducing the costs of implementing novel engine-based vehicles and power generation equipment since the distribution infrastructure of said low-cost chemicals to homes, buildings, and roads already exists.

The novel chemical composition transformation method and devices as described can be utilized to degrade undesirable species from a feed into more preferred form. Illustration include degradation of species such as toluene, methylethyl ketone, ethylene oxide, methylene chloride, formaldehyde, ammonia, methanol, formic acid, volatile organic vapors, odors, toxic agents, biomedical compounds into intermediates or final products such as carbon dioxide and water vapor. In another application, organics in liquid streams may be treated using these devices. Alternatively, novel chemical composition transformation devices as described can be utilized to remove and recover precious and strategic metals from liquid waste streams; or to remove hazardous metal ions from waste streams (waste water). The device can also be used to purify fluid streams by removing low concentrations of contaminants such as in preparing extremely pure water or extremely pure gases needed in semiconductor device manufacturing.

The invention can be applied to automatically and on-demand clean contaminants and stained surfaces such as windows in skyscrapers and hotels, and window shields of automobiles and aircraft. Stains are often organic in nature or comprises of substances that change the refractive index of a surface. A thin nanostructured coating of transparent ceramic or film (such as but not limiting to indium tin oxide, doped glasses, metals, and ceramics) can be deposited with electrodes printed connecting said film. The film can be part of an electrical circuit that is triggered on-demand to catalyze the substance in any stain on surface of interest. The invention may also be integrated in air conditioners, heating, and ventilation systems to clean air, or at-source and conveyors of emissions such as carpets, combustion chambers, and ducts. The teachings can also be utilized to build low-cost odor control systems inside microwaves, refrigerators, and portable or plug-in type odor removal devices at homes and offices. Odors are organic chemicals and preferred method of treating odors is to transform the chemicals responsible for odor into carbon oxide and moisture. The teachings contained herein can be applied to produced catalytic units that transform the chemicals responsible for odors into more desired products. Similarly, the teachings can yield devices to address the problems inside printers and photocopiers and other such office and industrial equipment that emit gases such as ozone and volatile chemicals.

The invention can enable the use of multifunctional equipment. An illustration of this, without limiting the scope, would be to coat the surface of a pipe with conducting formulation and then conduct the reaction while the raw material is been transported from source to some desired destination. The pipe in this case performs more than one function-it helps transport the feed and it also enables the reaction to occur during such transport.

The invention can be applied in membrane reactors, ion exchange units, catalytic distillation, catalytic separation, analytical instruments, and other applications that combine the benefits of catalysts with chemical unit operations known in the art.

This invention can also be utilized to develop and produce products that are based on catalytic or high surface area-based properties of materials used in the product. An illustrative, but not limiting, product of this type would be one that sense, react, trigger, or adapt to changes in environment in general, and in the chemical composition of a fluid in particular such as the teachings in commonly assigned U.S. patent application Ser. No. 09/074,534 and which is incorporated herewith. The invention can be generically applied to develop and produce products that sense, react, trigger, or adapt to changes in the environment such as changes in the thermal state, mechanical state, magnetic state, electromagnetic state, ionic state, optical state, photonic state, chromatic state, electronic state, biological state, or nuclear state, or a combination of two or more of these. In all cases, when the teachings contained herein are applied to a device in conjunction with electrical field, the benefit obtained is the modification of surface state of the active material and/or the modification in the property of the active material and/or the modification in the environment, as the said surface interacts with the environment.

As a non-limiting example, if the active layers are prepared from thermally sensitive material compositions, rapid response thermal sensors can be produced. In another example, if piezoelectric compositions are used in the active layer in a multilaminate stack, vibration and acceleration sensors can be produced. In yet another example, magnetic compositions can yield rapid response magnetic sensors and magnetoresistive sensors. If the active layer instead is prepared from compositions that interact with photons, novel chromatic, luminescent, photodetectors and photoelectric devices may be produced. With compositions interacting with nuclear radiation, sensors for detecting nuclear radiation may be produced. In another example, with biologically active layers, biomedical sensors may be produced. With insulating interlayers, these device may be thermally isolated or made safe and reliable. The active layers can be mixed, as discussed before, to provide multifunctional devices and products. The sensing layers may be cut or left intact for specific applications. The sensing layer may be just one layer or a multitude of as many layers as cost-effectively desirable for the application. The electrode may also be one layer or a multitude of as many layers as cost-effective and necessary for the application. These sensors have performance characteristics desired in chemical, metallurgical, environmental, geological, petroleum, glass, ceramic, materials, semiconductor, telecommunications, electronics, electrical, automobile, aerospace and biomedical applications. Such sensors can be combined with metrology techniques and transducers to produce smart products and products that adapt and learn from their environments.

EXAMPLE 1

Partial Oxidation of Methanol CASE I

A mixture of 75% ITO (15.7 $m^2$/g BET surface area) and 25% $Al_2O_3$ (61.7 $m^2$/g surface area) nanoparticles is formed by milling the two powders together. A slurry is prepared from this high surface area mixture in iso-propanol. An electroded porous (0.2–0.3 mm pores) honeycomb $Al_2O_3$ structures (3.8 cm×1.3 cm×0.6 cm) is dipped into the mixture. The electrodes are made of silver, although other conductive electrodes are expected to work as well. The sample is dried at room temperature. The catalyst is reduced in a flow through quartz tube reduction system in 5% H2 in Nitrogen at 350° C. After 30 minutes its resistance drops to about 1000 ohms, with a visible change of color to green-blue to light blue. The reduced or activated thin film is transferred to the reactor and is exposed to 100 ml/min of Methanol/Air vapor under a small electric field. The results of this experiment are tabulated in the following table.

TABLE 8

| Voltage (volts) | Current (amps) | Temp (° C.) | $H_2$ % | Conversion % MeOH |
|---|---|---|---|---|
| 95 | 0.15 | 225 | 17.5 | 80% |

Interestingly, the reaction produced less than 2% carbon monoxide. This example suggests that electrically activated catalysis can produce greater than 10% hydrogen from methanol and air at average substrate temperatures below 300° C. Alternatively, this example suggests that hydrogen can be produced from alcohols such as methanol with low concentrations of carbon monoxide.

EXAMPLE 2

Partial Oxidation of Methanol CASE II

The feed is preheated in this example by, for example, unit processes 103 shown in FIG. 1. The catalyst of Example 1 is treated to 60% oxygen/40% nitrogen that is saturated with methanol heated to 40° C. To prevent condensation of methanol, the feed line connecting the methanol tank and the reactor 104 is heated as well. The reaction is initiated with electrical current and then the current is switched off. Table 9 presents the results observed.

TABLE 9

| Voltage (volts) | Current (amps) | Temp (° C.) | $H_2$ % (wet) | Catalyst |
|---|---|---|---|---|
| 100 | 0.14 | 352 | 23% | Blue |
| 0 | 0 | 80 | 12% | Blue |

This example suggests that electrically activated catalysts in some reactions remain active even without the current. Hence, this invention may be used to activate catalysts in conditions that would not otherwise result in similarly activated catalyst. Alternatively, this example suggests that hydrogen can be produced from alcohols such as methanol with negligible input of power.

EXAMPLE 3

Methane Reforming CASE I

This example differs from Example 1 in that the feed is methane and water vapor. Methane (16% $CH_4$, 84% Nitrogen) is bubbled through warmed water in unit operations network 103 and this mix is fed into the reactor. The results are presented in Table 10.

TABLE 10

| Voltage (volts) | Current (amps) | Water Temp (° C.) | $H_2$ % | Catalyst gms |
|---|---|---|---|---|
| 85 | 0.05 | 65 | 1.2 | 0.29 |

This example suggests that electrically activated catalysts is not limited to methanol oxidation. It has broad impact application. Specially, this example shows that the technology may be used for hydrocarbon reforming.

EXAMPLE 4

Methane Reforming CASE II

A honeycomb surface was coated with indium tin oxide using sputtering process. Palladium acetate was applied to the surface such that it yield a continuous layer of palladium. The honeycomb catalyst was placed in a circuit and a voltage drop applied across the catalyst. This passage of current so resulting activated the catalyst. This activated catalyst was externally heated with a heating plate. Methane was passed over the catalyst along with water vapor and oxygen (as air) in the reactor system of example 1. The products from the reactor were primarily hydrogen and carbon dioxide. The observed carbon monoxide as measured by gas chromatograph was less than 2%, even though the hydrogen concentration was greater than 10%. This high hydrogen to carbon monoxide ratio (greater than 5) is highly unusual as conventional methane reforming produces greater than 10% carbon monoxide and the hydrogen to carbon monoxide ratio is less than 5. This examples suggests that electrically activated catalysis is useful in hydrocarbon reactions and that it may be used to produce hydrogen from hydrocarbons, water vapor and oxygen in a single step with low concentrations of carbon monoxide. The hydrogen so produced could be used, after suitable post-processing, as feed for fuel cells, merchant hydrogen, chemical and bio-chemical reactions, pharmaceutical synthesis, fuels for rockets, and for instrumentation applications.

EXAMPLE 5

Gas Storage with Electrically Activated Material

Gas storage and discharge is often a physisorption or chemisorption process. Gas storage applications exist in many situations—e.g. hydrogen, methane, gas purification, refrigeration cycles, batteries etc. While the teachings of the present invention can be applied to all gases, the particular example illustrates an embodiment for hydrogen storage applications.

Surface adsorbed and/or chemical hydrides are formed during hydrogen storage process. This process often requires thermal cycles. This can be provided by applying electro-magnetic field and passing electrical current through the material of interest. This can be accomplished because most alloys and hydrides offer reasonable electrically conductivity. The resistance of these materials changes with extent of hydrogen storage. With a circuit that determines the resistance of the storage bed, the hydrogen loading of a bed can be estimated. Thus this feature can also be used to systematically monitor and control the adsorption or desorption process. The flow of current, can through ohmic heating, change the temperature of the bed and this in turn can affect the discharge rates and extent. Application of electromagnetic field in general and the flow of current in particular is simpler, smaller, and more rapid than achieving temperature profile through the use of an external furnace. Such a technique can be useful for the storage of any gas. It is also anticipated that this process can be used to separate isotopes and processes that benefit from adsorption and/or desorption phenomena over surfaces.

Some specific illustrations of hydrogen storage materials include Mg 80%+$LaNi_5$ 20% amorphous/nanostructured composite materials, Mg—Ni—Ce, ZrNi—$Mg_2Ni$, $TiMn_{1.5}$, $TiMn_2$ based amorphous and amorphous/nanostructured composite materials, fullerenes, and $La_2Mg_{17}$ (66.6 wt %)+$LaNi_5$ (33.3 wt. %) . Pd, Pt, Ni, and V are potential additives for this application.

Reactor Variations

The reactor network 104 may be implemented using a continuous stirred-tank reactor (CSTR), plug-flow reactor (PFR), batch or any other form of reactor design. Process control and automation may be added to improve the process. The process control may be proportional (P), proportional-integral (PI), proportional integral derivative (PID), proportional-derivative (PD) or any other type. The reactor may comprise solid walls formed of a non-reactive material including ceramics, metals, polymers and the like selected to meet the chemical, mechanical and electrical needs of a particular application.

Figure 5A:
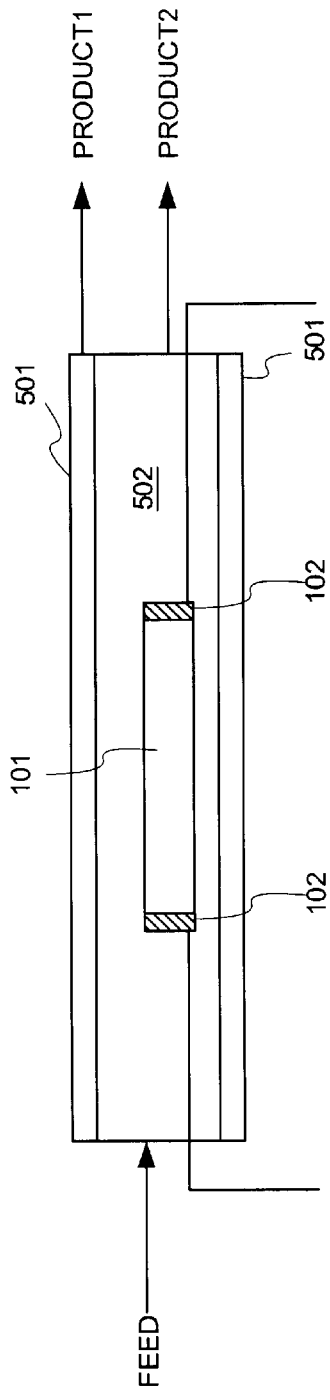
FIG. 5A and FIG. 5B illustrate an integrated device implementation in accordance with the present invention.
Figure 5B:
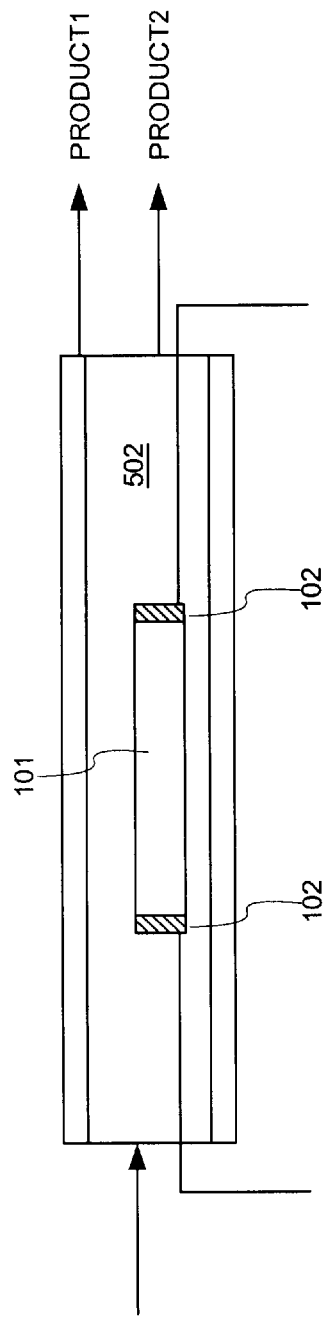

Alternatively, a membrane 501 replaces some or all of the reactor walls of the reactor 104 containing the electrically activated catalyst as shown schematically in FIG. 5A and FIG. 5B. The membrane can be functionally gradient type integrated into the reactor wall as shown in FIG. 5B, or simple layer type shown in FIG. 5A. Some of the products (e.g., Products 1 in FIG. 5A and FIG. 5B) that are formed in the vicinity of electrically activated catalyst 101 diffuse through membrane 501. The passage through membrane 501 enriches certain desired components within in the reactor 502 outside of the membrane 501.

Figure 6A:
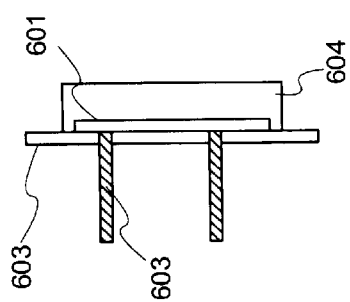
FIG. 6A shows a side view of an alternative embodiment structure for a chemical transformation device in accordance with the present invention.
Figure 6B:
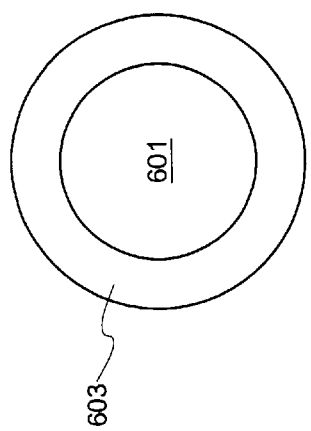
FIG. 6B shows a plan view of the embodiment shown in FIG. 6A.

FIG. 6A and FIG. 6B show an optional embodiment in which an electrically activated catalyst 601 is incorporated into a plug-in type device. As shown in FIG. 6A, catalyst 601 is on affixed to a supporting substrate 603 by lamination, adhesives, surface tension or other means. Catalyst 601 may be provided as a decal applied to substrate 603, or may be applied to substrate 603 by screen printing, evaporation, sputtering, or other thin or thick film techniques.

The device of FIG. 6A and FIG. 6B can be plugged into any electrical outlet such as conventional 110 or 220 volt AC mains power, or 12 volt DC power available in vehicles. Electromagnetic field is coupled to catalyst 601 by electrodes 602. In the specific embodiment, electrodes 602 pass through holes or plated vias through substrate 603. However, it is contemplated that printed conductors using printed circuit board and or ceramic module techniques may be readily applied to provide other electrical conduction configurations.

Alternatively, electronic and electrical circuit is incorporated to convert the electrical outlet voltage and current into more desirable magnitude or frequency of voltage and current for the device. Further, an electromagnetic field may be induced in catalyst 601 using, for example, radiating coils or antenna structures formed on one side of substrate 603 that produce electromagnetic field that penetrate to catalyst 601. Such a configuration, not shown, isolates exposed surfaces from electrical potentials to improve safety and convenience.

Preferably, a ventilated cover 604 is provided to mechanically protect the catalyst 601 while allowing environmental atmosphere to reach the surface of catalyst 601. Sensor(s) or timers or both may be added to improve functionality of the device. A sensor, for example, may be used to indicate the need to replace the device.

In operation, a polluted gas stream (e.g. air) diffuses into the cover, is catalytically remediated, and the benign products diffuse away from catalyst and through the cover. This device can destroy harmful gases, odor, biospecies, pathogens, etc.

Figure 7A:
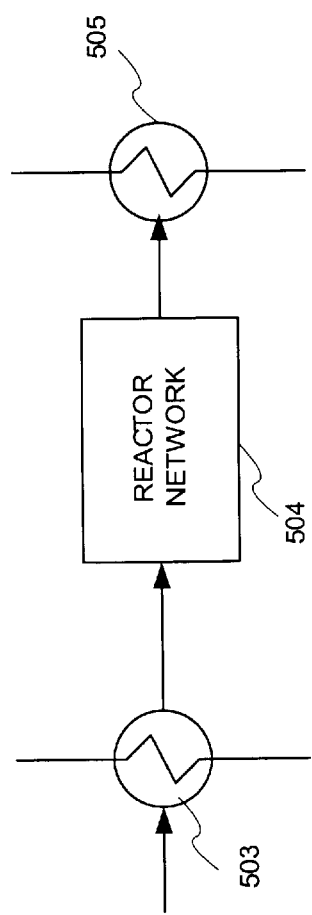
FIG. 7A and FIG. 7B illustrate further alternative embodiment structures for chemical transformation device in accordance with the present invention.
Figure 7B:
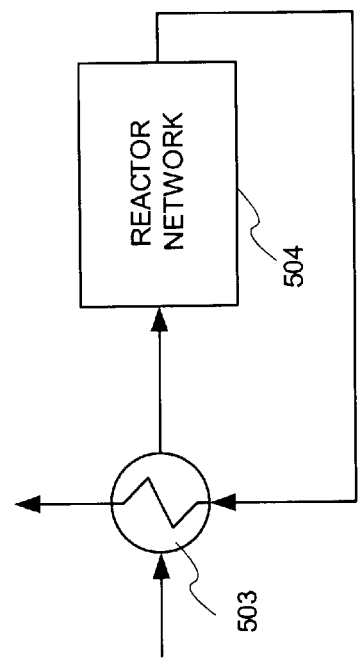

FIG. 7A and FIG. 7B illustrate an example configuration illustrating a manner in which the process components may be integrated. The process integration requires less equipment, has lower capital and operating costs, and is therefore preferable in some cases. However, sometimes, integrated process require better process monitoring and controls.

FIG. 7A is largely analogous to the process configuration shown in FIG. 1 where heat exchanges 703 and 705 are specific instances of unit operation networks 103 and 105 in FIG. 1. Functionally, heat exchangers 703 and 705 serve to add/remove heat from the feed stream and product stream, respectively. Heat exchanges are preferably implemented in a manner that provides acceptable flow without otherwise interfering with or impeding the feed stream and/or product stream. Heat exchanges 703 may comprise electrical or fuel powered heating elements, or obtain heat energy by other available heat source.

FIG. 7B shows an integrated configuration in which heat removed from the product stream is exchanged into the feed stream to provide energy efficient operation. A feed composition is preheated by heat exchanger 705 and passed to an electrically activated reactor 704 in accordance with the present invention. Electrically activated reactor 704 includes the catalyst 101 that while electrically activated, transforms the feed composition into the product composition. The heated product composition is passed to heat exchanger 705 for heat removal. Heat exchanger 705 in FIG. 7B is configured to isolate the feed stream from the product stream.

Figure 8:
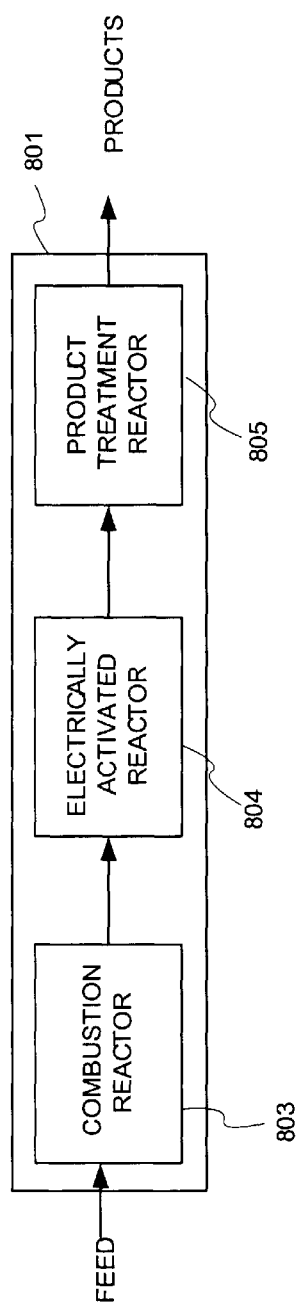
FIG. 8 illustrates in another alternative embodiment of a reactor in accordance with the present invention.

FIG. 8 presents an example in which the electrically activated reactor 804 is part of a reactor network 801. The first reactor 803 comprises a combustion reactor whose products enter the electrically activated catalyst reactor 804. The products from the catalyst reactor 804 then enter into another reactor 805 where the products are further reacted. The specificity of electrically activated catalyst reactor 804 enables a high degree of functional control over the products produced at each stage. For example, as described above the reaction environment of electrically activated reactor 804 can be carefully controlled to avoid secondary reactions that may produce uncontrolled or undesired reactions in downstream reactor 805. While the example of FIG. 8 illustrates only three reactors in series, a smaller or larger number of reactors can be used in series or parallel to produce desired substances.

Figure 9:
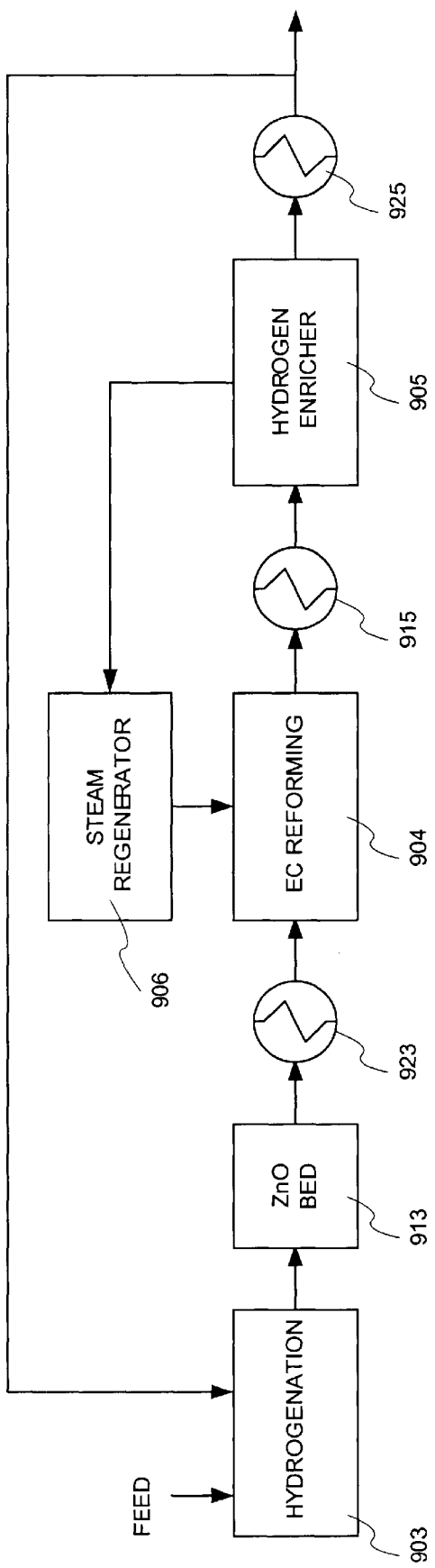
FIG. 9 shows in block diagram form a process in accordance with the present invention.

FIG. 9 illustrates one of the many embodiments of processes that can be designed around electrically activated catalysis. The reactor network of FIG. 9 is useful for the production of hydrogen from a feed stream comprising a hydrogen containing compound or compounds. Hydrogenation unit 903 receives the feed stream and preferably receives a portion of the hydrogen product. Hydrogenation unit 903 functions to combine free hydrogen with the feed composition to pre-treat unsaturated hydrocarbon compounds in the feed composition. The zinc oxide bed 913 provides a catalyst bed to promote the hydrogenation process. The products of the hydrogenation process are passed directly or after thermal repositioning by heat exchanger 923 to electrically activated catalyst (EC) reforming unit 904.

Reforming unit 904 performs a reaction such as described in example 3 and example 4 set out above to convert a hydrogen containing compound, such as methane, into hydrogen and byproducts such as carbon dioxide. Steam regenerator 906 supplies water vapor, which may be a byproduct of hydrogen enricher 905. The converted product is passed, optionally through heat exchanger 915 to postprocessing unit 905 that performs hydrogen enriching by removing water vapor and or other components of the converted product stream. Heat exchanger 915 operates to remove heat from the hydrogen stream generated by hydrogen enricher 905. The enriched hydrogen from the enricher can be sent into components such as fuel cell stack subsystem. The fuel processing subsystem in combination with fuel cell stack subsystem and power conditioning subsystem can be utilized for electricity generation applications.

While the examples herein do not show process control, process control mechanisms and techniques are widely known and applicable to the mechanisms shown in FIG. 9 to meet the needs of a particular application. For example temperature, pressure, flow rate, composition, voltage, current indicators or controllers may be added before, with, and after the electrically activated catalysis. This process begins with natural gas to produce hydrogen for fuel cells.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed. Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:

1. A method of modifying the performance of a composite material, the method comprising the acts of:

preparing at least two dissimilar component substances in a nanomaterial form; and placing the at least two nanomaterial component substances in proximity with each other to form a composite material such that the component substances share grain boundaries thereby inducing charge at the shared grain boundaries; wherein the induced charge modifies the performance of each component substance.

2. The method of claim 1 where the modified performance is a catalytic performance.

3. The method of claim 1 further comprising applying an external electric field.

4. The method of claim 1 wherein the performance of each component substance is modified by at least 5% in comparison with the performance of the component substance when the component substance is not placed in proximity with another of the dissimilar nanomaterial component substances.

* * * * *